US006426067B1

(12) United States Patent
Matthews et al.

(10) Patent No.: US 6,426,067 B1
(45) Date of Patent: Jul. 30, 2002

(54) ANGIOGENIC INHIBITORY COMPOUNDS

(75) Inventors: Barry Ross Matthews, Olinda; George Holan, Brighton, both of (AU)

(73) Assignee: Biomolecular Research Institute, Ltd., Parkville (AU)

( * ) Notice: Subject to any disclaimer, the term of this patent is extended or adjusted under 35 U.S.C. 154(b) by 0 days.

(21) Appl. No.: 09/230,188

(22) PCT Filed: Jul. 17, 1997

(86) PCT No.: PCT/AU97/00447

§ 371 (c)(1),
(2), (4) Date: Mar. 22, 2000

(87) PCT Pub. No.: WO98/03573

PCT Pub. Date: Jan. 29, 1998

(30) Foreign Application Priority Data

Jul. 17, 1996 (AU) .............................................. PO1044

(51) Int. Cl.$^7$ .............................................. A61K 31/74
(52) U.S. Cl. ............................. 424/78.08; 424/DIG. 16
(58) Field of Search ........................... 424/78.08, 78.18, 424/78.27, 78.29

(56) References Cited

U.S. PATENT DOCUMENTS

| 4,289,872 A | * | 9/1981 | Denkewalter et al. ...... 528/328 |
| 4,410,688 A | | 10/1983 | Denkewalter et al. ...... 528/328 |
| 4,507,466 A | | 3/1985 | Tomalia et al. ............. 528/332 |
| 4,558,120 A | | 12/1985 | Tomalia et al. ............. 528/363 |
| 4,568,737 A | | 2/1986 | Tomalia et al. ............. 528/310 |
| 4,587,329 A | | 5/1986 | Tomalia et al. ............. 528/363 |
| 5,593,664 A | * | 1/1997 | Wright et al. ............ 424/78.08 |

FOREIGN PATENT DOCUMENTS

| GB | 2 260 134 | 4/1993 |
| JP | 7-267879 | 10/1995 |
| WO | WO 94/04165 | 3/1994 |
| WO | WO 95/24907 | 9/1995 |
| WO | WO 95/34595 | 12/1995 |

OTHER PUBLICATIONS

Roy, R., et al., "Solid–Phase Synthesis of Dendritic Sialoside Inhibitors of Influenza A Virus Haemagglutinin," J. Chem. Soc., Chem. Commun., pp. 1869–1872 (1993).

* cited by examiner

*Primary Examiner*—Jose' G. Dees
*Assistant Examiner*—Konata M. George
(74) *Attorney, Agent, or Firm*—Foley & Lardner

(57) ABSTRACT

For proposes of prophylactic or treatment of diseases related to inappropriate angiogenesis, a compound can be administered that is (i) a linear, non-carbohydrate polymer having a plurality of side chain groups or (ii) a dendrimer having a plurality of terminal groups. At least one of the side chain groups of the linear, non-carbohydrate polymer has an anionic- or cationic-containing moiety bonded or linked thereto. The plurality of terminal groups of the dendrimer has at least one anionic- or cationic-containing moiety bonded or linked thereto.

26 Claims, No Drawings

ANGIOGENIC INHIBITORY COMPOUNDS

This application is a 371 of PCT/AU97/00447, filing on Jul. 17, 1997.

FIELD OF THE INVENTION

This invention relates to compounds which are effective in inhibition of angiogenesis, and accordingly can be used instead of sulfated polysaccharides such as heparin in preventing restenosis, accelerating wound healing, and in inhibiting tumor cell metastasis.

BACKGROUND OF THE INVENTION

The use of sulfated polysaccharides in the inhibition of angiogenesis and in the treatment of disorders and conditions associated with angiogenesis has been previously disclosed. Thus, International Patent Application No. PCT/GB95/00515 (WO 95/24907), the contents of which are incorporated herein by reference, discusses the use of heparin and other sulfated polysaccharides such as pentosan polysulfate and dextran sulfate in treatment of these disorders and conditions, and discloses the use of another sulfated polysaccharide, laminarin sulfate, which exhibits only about 30% of the anti-coagulant activity of heparin, in preventing restenosis by the inhibition of vascular smooth muscle cell proliferation, in accelerating wound healing by activating the release of active growth factors stored in the extracellular matrix, and for inhibiting tumor cell metastasis by inhibition of heparanase activity.

International Patent Application No. PCT/AU95/00350 (WO 95/34595) discloses a class of antiviral compounds comprising a dendrimer such as a polyamidoamine or polylysine dendrimer having a plurality of terminal groups, wherein at least one of the terminal groups has an anionic- or cationic-containing moiety bonded or linked thereto, particularly a sulfonic acid-containing, a carboxylic acid-containing, or a trimethyl-ammonium-containing moiety.

The present invention provides the use of polyionic materials formed by linking ionic groups to a linear non-carbohydrate polymer or a dendritic polymer in the inhibition of angiogenesis and in the treatment of related disorders and conditions.

SUMMARY OF THE INVENTION

According to the present invention, there is provided a method of prophylactic or therapeutic inhibition of angiogenesis in a human or non-human animal patient, which comprises administration to the patient of an effective amount of a compound selected from:

(i) linear, non-carbohydrate polymers having a plurality of side chain groups wherein at least one of said side chain groups has an anionic- or cationic-containing moiety bonded or linked thereto; and (ii) dendrimers having a plurality of terminal groups wherein at least one of said terminal groups has an anionic- or cationic-containing moiety bonded or linked thereto.

Particularly preferred compounds for use in the method of the present invention are linear polymers having sulfonic acid-containing moieties, carboxylic acid-containing moieties, phosphoric or phosphonic acid-containing moieties, boronic acid-containing moieties, neuraminic or sialic acid-containing moieties or moieties containing neuraminic or sialic acid modified in the 4- or other position thereof, linked to side chain groups thereof, and dendrimers having sulfonic acid-containing moieties, carboxylic acid-containing moieties, phosphoric or phosphonic acid-containing moieties, boronic acid-containing moieties, neuraminic or sialic acid-containing moieties or moieties containing neuraminic or sialic acid modified in the 4- or other position thereof, linked to terminal groups thereof.

The compounds used in the method of this invention are referred to herein are linear polyionic polymers or polyionic dendrimers, respectively, and these terms are used throughout this specification and the claims which follow to include not only the polymers or dendrimers per se, but also their pharmaceutically or veterinarily acceptable salts, for example the alkaline metal or alkaline earth metal salts such as the sodium, potassium or calcium salts.

DETAILED DESCRIPTION OF THE INVENTION

Preferred compounds used in accordance with the present invention include (i) linear polyionic polymers of the general formula I:

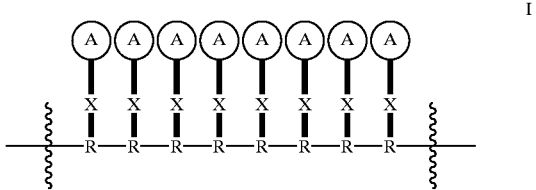

wherein:
R is a non-carbohydrate monomer unit forming a linear polymer backbone;
X is an optional linking group on the side chain groups of monomer units R; and
A is an anionic-containing moiety; and (ii) polyionic dendrimers of the general formula II:

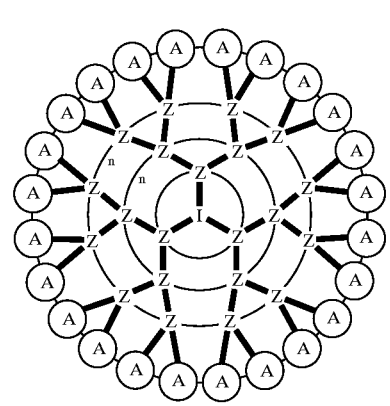

wherein:
I is an initiator core;
Z is an interior branching unit;
n is an integer which represents the number of generations of the dendrimer; and
A is an anion-containing moiety which may be linked to interior branching unit Z through an optional linking group X.

In accordance with the present invention, the preferred linear polyionic polymers are polyanionic materials formed by the conjugation of anionic moieties (A) to a linear non-carbohydrate polymer backbone (made up of a plurality of monomer units R), optionally through linking groups (X). The resultant polyanionic linear polymers have a weight range distribution of repeating units to give a desired median range of molecular weight distribution. Desirably, the median range of molecular weight distribution is from 1,000 to 1,000,000, preferably from 10,000 to 600,000.

The monomer unit R is preferably an amino or amide moiety, more preferably an amino acid moiety. A particularly preferred monomer unit is a lysine moiety. Poly-L-lysines having various molecular weight ranges are available commercially from Sigma Chemical Company.

The anionic moiety A can be linked to reactive side chain groups on the linear polymer backbone either directly or via a variety of functional linking groups X such as, but not limited to, esters, amides, ethers, thioethers, amines, ureas, thioureas, carbamates and carbonates.

The optional linking group X may also act as a spacer between the polymer and the anionic moiety A, and may consist of an alkyl chain (optionally substituted or branched), an alkoxy, polyalkoxy, alkylthio or polyalkylthio chain (optionally substituted), or an alkenyl, multiple alkenyl, alkynyl or multiple alkynyl chain (optionally substituted). Suitable spacer chains include groups of the formula —$(CH_2)_n$—Z—$(CH_2)_n$—, wherein Z is —$CH_2$—, —CH=CH—, —C≡C—, —O— or —S—, and n is an integer of from 1 to 15.

Dendrimers are macromolecular highly branched compounds formed by reiterative reaction sequences starting from an initial, core molecule with successive layers or stages being added in successive "generations" to build up a three-dimensional, highly ordered polymeric compound. Dendrimers are characterised by the following features: I an initiator core(I) which may have one or more reactive sites and be point-like or of significant size so as to effect the final topology of the dendrimer; ii layers of branched repeating units (Z) attached to the initiator core; iii functional terminal groups (such as anionic moieties A) attached to the surface of the dendrimer, optionally through linking groups (such as linking groups X described above). The present invention uses dendritic structures as frameworks for the attachment of ionic moieties; the invention is not limited to the spherical dendrimers described in detail herein but can be based on any dendritic structure. The variety of dendrimers in both shape and constitution are well known to persons skilled in the art.

The preparation of dendrimers is well known, and is described by way of example in U.S. Pat. Nos. 4,289,872 and 4,410,688 (describing dendrimers based on layers of lysine units), as well as U.S. Pat. Nos. 4,507,466, 4,558,120, 4,568,737 and 4,587,329 (describing dendrimers based on other units including polyamidoamine or PAMAM dendrimers). The dendrimers disclosed in these US patents are described as being suitable for uses such as surface modifying agents, as metal chelating agents, as demulsifiers or oil/water emulsions, wet strength agents in the manufacture of paper, and as agents for modifying viscosity in aqueous formulations such as paints. It is also suggested in U.S. Pat. Nos. 4,289,872 and 4,410,688 that the dendrimers based on lysine units can be used as substrates for the preparation of pharmaceutical dosages.

International Patent Publications Nos. WO 88/01178, WO 88/01179 and WO 88/01180 disclose conjugates in which a dendrimer is conjugated or associated with another material such as a carried pharmaceutical or agricultural material. In addition, International Patent Publication No. WO 95/24221 discloses dendritic polymer conjugates composed of at least one dendrimer in association with a carrier material which can be a biological response modifier, and optionally a target director. These patent publications together with the U.S. patents mentioned above contain a broad disclosure of various dendrimers and processes for the preparation thereof, and the disclosure of each of these publications is incorporated herein by reference.

The term "dendrimer" as used herein is to be understood in its broadest sense, and to include within its scope all forms and compositions of these dendrimers as disclosed in Patent Publications Nos. WO 88/01178, WO 88/01179 and WO 88/01180. The term also includes linked or bridged dendrimers as disclosed in these patent publications.

The preferred dendrimers of the present invention comprise a polyvalent core covalently bonded to at least two dendritic branches, and preferably extend through at least two generations. Particularly preferred dendrimers are polyamidoamine (PAMAM) dendrimers, PAMAM (EDA) dendrimers and polylysine dendrimers.

In accordance with the present invention, at least one, and preferably a substantial number, of the side chain groups on the linear polymer or terminal groups on the surface of the dendrimer has an anionic- or cationic-containing moiety covalently bonded thereto. The side chains of the linear polymer or branches of the dendrimer may terminate in amino groups or other functional reactive groups such as OH, SH, or the like, which subsequently can be reacted with the anionic or cationic moieties. Where the side chain groups of the linear polymer or terminal groups of the dendrimer are amine groups, the anionic- or cationic-containing moiety may be linked to the dendrimer by a variety of functional groups including amide and thiourea linkages. Preferred anionic- or cationic-containing moieties which may be bonded to the side chain groups of the linear polymer or terminal groups of the dendrimer include sulfonic acid-containing moieties, carboxylic acid-containing moieties (including neuraminic and sialic acid-containing moieties and modified neuraminic and sialic acid-containing moieties), boronic acid-containing moieties, phosphoric and phosphonic acid-containing moieties (including esterified phosphoric and phosphonic acid-containing moieties) and trimethylammonium-containing moieties.

Suitable anionic- and cationic-containing moieties which may be bonded or linked to the amino or other side chain or terminal groups include, by way of example, the following groups (in which n is zero or a positive integer, more particularly n is zero or an integer of from 1 to 20):

—$NH(CH_2)_nSO_3^-$ —$(CH_2)_nSO_3^-$ —$Ar(SO_3^-)_n$
—$CH_2CH(SO_3^-)COOH$ —$CH(SO_3^-)CH_2COOH$ —ArX$(CH_2)_nSO_3^-$ X=O, S, NH

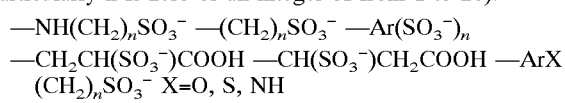

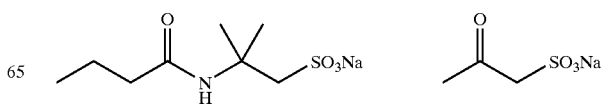

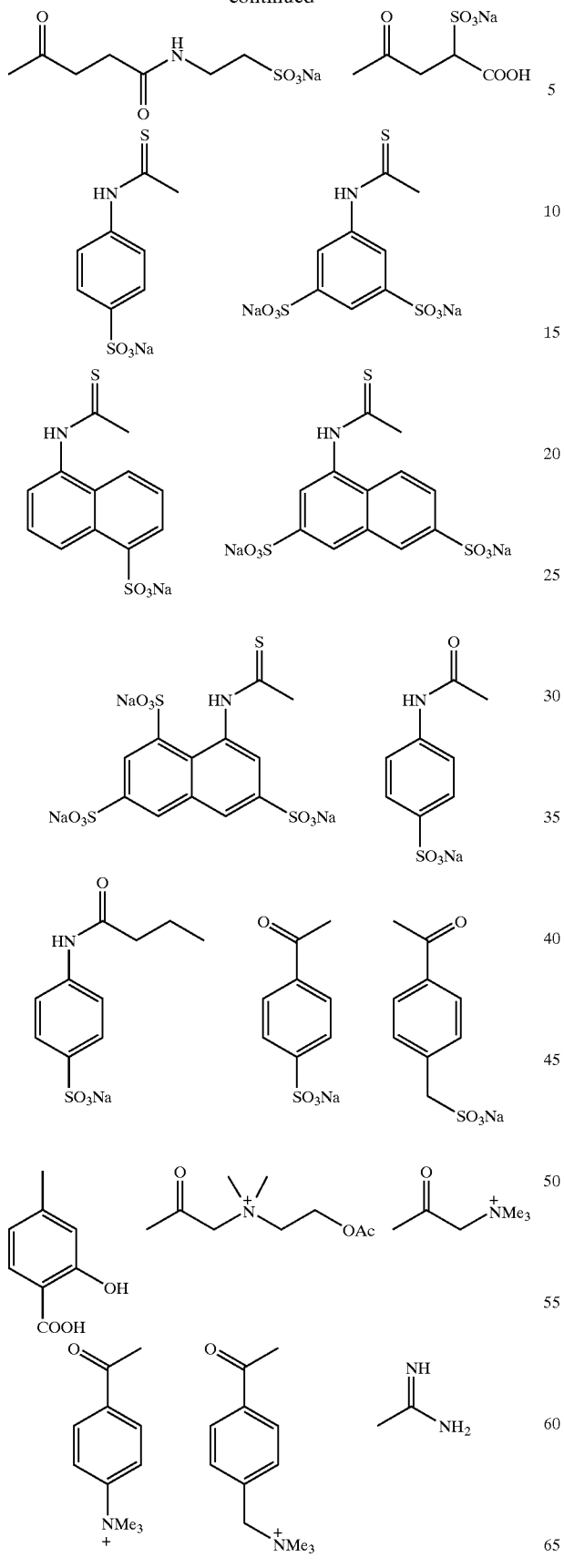
—ArXP(=O)(OR)$_2$ X=O, CH$_2$, CHF, CF$_2$ R=alkyl, aryl, H, Na,
—ArXP(=O)(OR$^1$)(NR$^2$R$^3$) X=O, CH$_2$, CHF, CF$_2$ R$^1$=alkyl, aryl, H, Na R$^2$, R$^3$=alkyl, aryl
—Ar[P(=O)(OR)$_2$]$_n$ R=alkyl, aryl, H, Na n=1–3
—Ar[B(OH)$_2$]$_n$ n=1–3 —Ar[COOH]$_n$ n=1–3

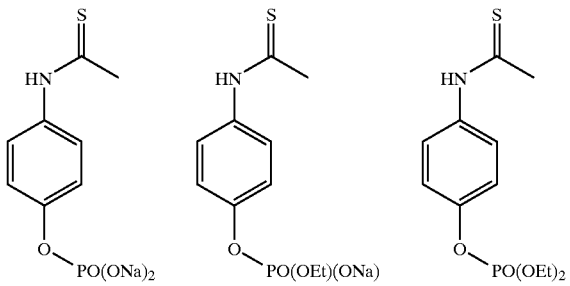

In addition to the above, various neuraminic or sialic acid-containing moieties or modified neuraminic or sialic acid-containing moieties may be bonded or linked to the side chain or terminal groups in accordance with this invention. These moieties include the various N- and O-substituted derivatives of neuraminic acid, particularly N- and O-acyl derivatives such as N-acetyl, O-acetyl and N-glycolyl derivatives, as well as moieties in which the neuraminic acid group is modified, particularly by substitution in the 4-position, with an amino, amido, cyano, azido or guanidino group.

The anionic or cationic linear polymers and dendrimers of this invention may be prepared by standard chemical methods which are well known to persons skilled in this art. Suitable methods are described by way of the example in Examples below.

As previously described, the anionic or cationic linear polymers and dendrimers of the present invention have been found to inhibit angiogenesis. Accordingly, the method of the present invention includes inhibition of angiogenesis in a patient, treatment of conditions where growth of new blood vessels is involved such as chronic inflammation, diabetic retinopathy, psoriasis and rheumatoid arthritis, as well as treatment of related disorders and conditions including, but not limited to, prevention of restenosis by inhibition of vascular smooth muscle cell proliferation, acceleration of wound healing by activation of the release of active growth factors stored in the extracellular matrix, and inhibition of tumor cell metastasis by inhibition of angiogenesis.

Thus, in another aspect the present invention provides a pharmaceutical or veterinary composition for prophylactic or therapeutic inhibition of angiogenesis in a human or non-human animal patient, which comprises an anionic or cationic linear polymer or dendrimer as broadly described above, in association with at least one pharmaceutically or veterinarily acceptable carrier or diluent.

The formulation of such compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences,* 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

In yet another aspect, this invention provides the use of an effective amount of an anionic or cationic linear polymer or dendrimer as broadly described above in the prophylactic or therapeutic treatment of, or in the manufacture of a medicament for prophylactic or therapeutic treatment of a human or non-human animal patient by inhibition of angiogeneis.

A variety of administration routes are available. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral, rectal, topical, nasal, inhalation, transdermal or parenteral (e.g. subcutaneous, intramuscular and intravenous) routes. Formulations for oral administration include discrete units such as capsules, tablets, lozenges and the like. Other routes include intrathecal administration directly into spinal fluid, direct introduction such as by various catheter and balloon angioplasty devices well known to those of ordinary skill in the art, and intraparenchymal injection into targeted areas.

The compositions may conveniently be presented in unit dosage form and may be prepared by any of the methods well known in the art of pharmacy. Such methods include the step of bringing the active component into association with a carrier which constitutes one or more accessory ingredients. In general, the compositions are prepared by uniformly and intimately bringing the active component into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the active component, in liposomes or as a suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. In addition, fatty acids such as oleic acid find use in the preparation of injectables.

The active component may also be formulated for delivery in a system designed to administer the active component intranasally or by inhalation, for example as a finely dispersed aerosol spray containing the active component.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer. In addition, a pump-based hardware delivery system can be used, some of which are adapted for implantation.

The active component is administered in prophylactically or therapeutically effective amounts. A prophylactically or therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

Generally, daily oral doses of active component will be from about 0.01 mg/kg per day to 1000 mg/kg per day. Small doses (0.01–1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of compounds.

The active component according to the invention may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced into the udder via the teat;

(c) topical application, e.g. as a cream, ointment or spray applied to the skin; or (d) intravaginally, e.g. as a pessary, cream or foam.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Further features of the present invention will be apparent from the following Examples which are included by way of illustration, not limitation of the invention. In the following Examples, PAMAM dendrimers refer to polyamidoamine dendrimers based on an ammonia core as detailed in U.S. Pat. Nos. 4,507,466, 4,558,120, 4,568,737 and 4,587,329; PAMAM (EDA) dendrimers refer to polyamidoamine dendrimers based on an ethylene diamine core; and $BHAlys_x\text{-}lys_y lys_z$ dendrimers refer to polylysine unsymmetrical dendrimers based on a benzhydrylamine core and lysine branching units as described in U.S. Pat. Nos. 4,289,872 and 4,410,688. The polyamidoamine dendrimers PAMAM 1.0, PAMAM 2.0, PAMAM 3.0, PAMAM 4.0, PAMAM 5.0 or higher generation, PAMAM 4.0 (EDA), and the polylysine dendrimers $BHAlyslys_2$, $BHAlyslys_2lys_4$, $BHAlyslys_2lys_4lys_8$ and $BHAlyslys_2lys_4lys_8lys_{16}$, $BHAlyslys_2lys_4lys_8lys_{16}lys_{32}$, $BHAlyslys_2lys_4lys_8lys_{16}lys_{32}lys_{64}$, or higher generations prepared as described in U.S. Pat. Nos. 4,289,872, 4,410,688, 4,507,466, 4,558,120, 4,568,737 and 4,578,239 and International Patent Publications Nos. WO 88/01178, WO 88/01179, WO 88/01180 and WO 95/24221 referred to above.

EXAMPLE 1

Reaction of Dendritic Polymers with 2-acrylamido-2-methyl Propane Sulfonic Acid to give Sulfonic Acid Terminated Dendrimers

A PAMAM 1.0

Solid sodium carbonate (0.13 g; 1.0 mmol) was added slowly to a stirred solution of 2-acrylamido-2-methyl propane sulfonic acid (0.41 g; 2.0 mmol) in water (3 ml). After the evolution of gas had ceased, the pH of the solution was 8.0. A solution of PAMAM 1.0 (0.12 g; 0.33 mmol) in water (1 ml) was then added to the solution followed by the addition of four drops of a 40% aq. solution of benzyl trimethylammonium hydroxide. The solution was then heated under nitrogen at 60° for three days and then concentrated. The residue was purified by gel filtration (Sephadex G10; water) and then freeze dried to give the sulfonated PAMAM 1.0 dendrimer as an off white solid (0.51 g). $^1H$ and $^{13}C$ nmr spectra showed a mixture of dialkylated and monoalkylated PAMAM 1.0 dendrimer (ca. 70:30). $^{13}C$ nmr ($D_2O$): δ31.0, 31.1, 37.1, 37.7, 41.3, 48.6, 51.5, 53.1, 53.4, 55.6, 56.2, 61.2, 61.5, 178.3, 179.0, 179.8.

B PAMAM 2.0

PAMAM 2.0 was reacted with 2-acrylamido-2-methyl propane sulfonic acid as described above. The crude product was purified by gel filtration (Sephadex G10; water) and then freeze dried to give an off white solid. $^1H$ and $^{13}C$ nmr spectra showed a mixture of dialkylated and monoalkylated PAMAM 2.0 dendrimer (ca. 65:35). $^{13}C$ nmr ($D_2O$): δ31.0, 31.1, 37.1, 37.7, 41.3, 48.7, 51.5, 53.4, 55.6, 56.2, 61.2, 61.5, 178.4, 179.0, 179.1, 179.6.

When the above reaction was repeated omitting the benzyltrimethylammonium hydroxide a similar result was obtained.

C PAMAM 3.0 BRI2783

PAMAM 3.0 was reacted with 2-acrylamido-2-methyl propane sulfonic acid as above except that a slight excess of sodium carbonate was used and the benzyltrimethylammonium hydroxide was omitted. $^1H$ and $^{13}C$ nmr spectra showed a mixture of dialkylated and monoalkylated PAMAM 3.0 dendrimer (ca. 50:50). $^{13}C$ nmr ($D_2O$): δ31.0, 31.1, 36.9, 37.4, 41.1, 48.6, 51.5, 53.4, 55.7, 56.2, 61.1, 61.5, 178.2, 178.9, 179.0, 179.8.

D PAMAM 4.0 BRI2784

PAMAM 4.0 was reacted with 2-acrylamido-2-methyl propane sulfonic acid as described for PAMAM 3.0. $^1$H and $^{13}$C nmr spectra showed a mixture of dialkylated and monoalkylated PAMAM 4.0 dendrimer (ca. 35:65). $^{13}$C nmr (D$_2$O): δ31.0, 31.1, 36.9, 37.3, 41.1, 48.5, 51.5, 53.5, 55.7, 56.2, 61.1, 61.5, 178.1, 178.9, 179.0, 179.8.

EXAMPLE 2

Preparation of Sodium Sulfoacetamide Terminated Dendrimers

A PAMAM 1.0

A solution of 4-nitrophenyl bromoacetate (0.40 g; 1.5 mmol) in dry DMF (1 ml) was added to a stirred solution of PAMAM 1.0 (0.18 g; 0.5 mmol) in DMF (3 ml). The resulting yellow solution was stirred for 20 hours at room temperature, when a ninhydrin test was negative. The solution was concentrated (30°/0.1 mmHg) to give a yellow oil. This oil was partitioned between water and chloroform and the aqueous layer separated and washed with chloroform (2×) and finally with ethyl acetate. The aqueous solution was concentrated (35°/25 mmHg) to give the bromoacetylated PAMAM 1.0 dendrimer as a yellow oil (0.36 g; 100% ). $^{13}$C nmr (D$_2$O): δ32.8, 33.3, 43.0, 43.5, 54.4, 174.5, 176.4.

A solution of sodium sulfite (0.2 g; 1.6 mmol) in water (1 ml) was added to a solution of the bromoacetylated PAMAM 1.0 dendrimer described above (0.36 g; 0.5 mmol) in water (5 ml) and the solution left to stand at room temperature for eleven days. The yellow solution was concentrated to give a yellowish solid (0.60 g). $^{13}$C nmr (D$_2$O): δ34.4, 43.1, 43.4, 54.0, 61.7, 171.3, 177.2.

The above reaction sequence could be carried out without isolating the bromoacetylated dendrimer by simply adding the sodium sulfite solution to the crude aqueous extract obtained from the first reaction.

B PAMAM 2.0

Method 1

A solution of 4-nitrophenyl bromoacetate (0.18 g; 0.7 mmol) in dry DMF (1 ml) was added to a stirred solution of PAMAM 2.0 (0.10 g; 0.1 mmol) in DMF (3 ml). The resulting yellow solution was stirred for 20 hours at room temperature, when a ninhydrin test was negative. The solution was then added with swirling to water (150 ml) and the mixture extracted with chloroform (3×) and ethyl acetate. A solution of sodium sulfite (0.1 g; 0.8 mmol) in water (1 ml) was added to the crude bromoacetylated dendrimer solution and the mixture allowed to stand for three days at room temperature. The yellowish solution was then concentrated to give a yellow solid residue, which was purified by gel filtration (Sephadex LH20; water) to give the sodium sulfoacetamide terminated PAMAM 2.0 dendrimer (103 mg). $^{13}$C nmr (D$_2$O): δ33.0, 35.7, 36.0, 37.7, 40.3, 43.0, 43.2, 53.4, 53.7, 56.0, 61.6, 171.2, 174.6, 178.5.

Method 2

Solid succinimidyl acetylthioacetate (67 mg; 0.33 mmol) was added to a solution of PAMAM 2.0 (52 mg; 0.05 mmol) in dry DMF (2 ml) and the resulting solution stirred at room temperature for two days. The mixture was then concentrated (30°/10$^{31}$ $^3$ mmHg) to give an oily residue. The residue was partitioned between water and chloroform, and the water layer separated and concentrated to give a viscous oil (117 mg). $^1$H and $^{13}$C nmr showed the oil to be a mixture of the acylated dendrimer and N-hydroxy succinimide. Gel filtration (Sephadex G10; water) provide a pure sample of the acetylthioacetamide terminated PAMAM 2.0 dendrimer (29 mg). $^{13}$C nmr (D$_2$O): δ8 34.0, 34.2, 37.3, 43.0, 43.1, 43.3, 53.5, 54.0, 56.3, 175.4, 177.2, 177.5.

A solution of the above functionalised dendrimer in 40% aqueous formic acid (7 ml) was then added to an ice cold freshly prepared solution of performic acid (1.6 mmol) in formic acid (2 ml). The mixture was stirred for one hour at 0° and then for twenty hours at room temperature. A small amount of activated charcoal was then added to decompose any excess peracid, the mixture stirred for 30 minutes then filtered and concentrated to give a viscous oil.

The crude product was dissolved in water, the pH adjusted to 9.0 with aqueous sodium bicarbonate and the material desalted by passage through a column of Sephadex G10. A white solid (20 mg;) was obtained after lyophylisation which was spectroscopically essentially the same as the material obtained by method 1. $^{13}$C nmr (D$_2$O): δ33.0, 38.7,42.9, 43.0, 43.1, 53.9,54.3, 56.5, 61.6, 171.2, 176.4, 177.0.

EXAMPLE 3

Preparation of Sodium Sulfosuccinamic Acid Terminated Dendrimers

A PAMAM 1.0

Solid maleic anhydride (0.11 g; 1.1 mmol) was added to a stirred solution of PAMAM 1.0 (0.12 g; 0.33 mmol) in dry DMF (3 ml). The mixture became a little warm and brownish as the anhydride dissolved and the resulting solution was stirred overnight at room temperature. The solution was then concentrated (30°/10$^{-4}$ mmHg) to give a viscous oil. $^1$H and $^{13}$C nmr (D$_2$O) showed complete conversion of the PAMAM 1.0 to the trisamide together with some maleic acid. $^{13}$C nmr (D$_2$O): δ33.1, 42.8, 43.1, 54.3, 135.0, 137.1, 169.1, 171.9, 173.3.

The crude trisamide was then dissolved in water (4 ml) and solid sodium sulfite (0.20 g; 1.6 mmol) added. The resulting solution was allowed to stand at room temperature for four days and then concentrated. $^1$H and $^{13}$C nmr (D$_2$O) showed a 1:1 mixture of the regioisomeric sodium sulfosuccinamic acid terminated PAMAM 1.0 dendrimers together with some sulfosuccinic acid. The crude product was purified by gel filtration (Sephadex G10; water) to afford a sample of the sodium sulfosuccinamic acid terminated PAMAM 1.0 dendrimers (107 mg). $^{13}$C nmr (D$_2$O): δ33.3, 39.6, 40.0, 42.9, 43.1, 54.0, 67.9, 69.4, 173.8, 176.3, 177.6, 181.8.

B PAMAM 2.0

A mixture of the regioisomeric sodium sulfosuccinamic acid terminated PAMAM 2.0 dendrimers was prepared as described above. $^{13}$C nmr PAMAM 2.0 maleamic acid derivative (D$_2$O): δ32.8, 33.0, 38.7, 42.9, 53.8, 54.3, 56.5, 135.2, 136.8, 169.2, 171.9, 173.5, 174.6. $^{13}$C nmr PAMAM 2.0 sodium sulfosuccinamic acid derivatives (D$_2$O): δ37.0, 40.1, 41.1, 43.0, 43.2, 43.9, 53.0, 53.3, 55.5, 68.0, 69.4, 173.8, 177.6, 179.1, 179.5, 179.8, 182.3.

C PAMAM 4.0 BRI6038

Solid maleic anhydride (60 mg; 0.6 mmol) was added to a stirred solution of PAMAM 4.0 (51 mg; 0.01 mmol) in dry DMF (2 ml). The mixture initially became cloudy but soon gave a clear solution which was stirred overnight at room temperature. The solution was then concentrated (35°/10$^{-4}$ mmHg) to give a viscous oil. $^1$H and $^{13}$C nmr (D$_2$O) showed complete conversion of the PAMAM 4.0 to the polyamide together with some maleic acid. The crude polyamide was then dissolved in water (2 ml) and a solution of sodium sulfite (126 mg; 1.0 mmol) in water (2 ml) added. The resulting solution was allowed to stand at room temperature for two days and then concentrated. $^1$H and 13C nmr (D$_2$O) showed a mixture of the regioisomeric sodium sulfosuccinamic acid terminated PAMAM 4.0 dendrimers together with some sulfosuccinic acid. The crude product was purified by gel filtration (Sephadex LH20; water) to afford a sample of PAMAM 4.0 terminated with 24 regioisomeric sulfosuccinamic acid groups (90 mg). $^1$H nmr (D$_2$O): δ2.4–2.6; 2.7–3.1; 3.2–3.4; 3.9–4.0. $^{13}$C nmr (D2O): δ36.2; 39.8; 40.5; 43.0; 43.2; 53.5; 55.8; 68.1; 69.5; 173.8; 177.4; 177.6; 178.7; 182.3.

EXAMPLE 4

Preparation of Sodium N-(2-sulfoethyl)succinamide Terminated Dendrimers a Preparation of tetrabutylammonium N-(2-sulfoethyl) succinamic acid Solid succinic anhydride (0.5 g; 5.0 mmol) was added to a stirred solution of tetrabutylammonium 2-aminoethylsulfonic acid (1.83 g; 5.0 mmol) in dry dichloromethane (30 ml). The succinic anhydride slowly dissolved and the resulting cloudy solution was stirred overnight at room temperature. The mixture was filtered and the filtrate concentrated to give a viscous oil (2.41 g). $^{13}$C nmr showed complete conversion to the desired monoamide together with a small amount of succinic acid. Repeated precipitation of the product by dropwise addition of a dichloromethane solution to a large excess of diethyl ether gave tetrabutylammonium N-(2-sulfoethyl)succinamic acid as a white solid (1.762 g; 76% ), mp 125–127° C. $^1$H nmr (CDCl$_3$): δ0.86 (t, 12h, 4×CH$_3$), 1.28 (m, 8H, 4×CH$_2$), 1.50 (m, 8H, 4×CH$_2$), 2.33 (m, 2H, CH$_2$COOH), 2.44 (m, 2H, CH$_2$CONH), 2.76 (m, 2H, CH$_2$NHCO), 3.12 (m, 8H, 4×CH$_2$N), 3.50 (m, 2H, CH$_2$SO$_3^-$), 7.53 (br t, 1H, NH). $^{13}$C nmr (CDCl$_3$): δ13.5, 19.5, 23.8, 30.1, 30.9, 35.6, 50.0, 58.5, 172.0, 174.1.

b Preparation of Tetrabutylammonium 4-nitrophenyl N-(2-sulfoethyl)succinamate

A solution of dicyclohexylcarbodiimide (45 mg; 0.22 mmol) in dry dichloromethane (1 ml) was added to a stirred solution of tetrabutylammonium N-(2-sulfoethyl) succinamic acid (94 mg; 0.20mmol) in dichloromethane (2 ml), and the mixture stirred overnight at room temperature. The resulting suspension was filtered and the filtrate concentrated to give the crude active ester, which was used without further purification.

A Preparation of Sodium N-(2-sulfoethyl)succinamide Terminated PAMAM Dendrimers

PAMAM 4.0 BRI2786

A solution of the crude tetrabutylammonium 4-nitrophenyl N-(2-sulfoethyl)succinamate (0.30 mmol) in dry DMF (1 ml) was added to a stirred solution of PAMAM 4.0 (51.5 mg; 0.01 mmol) dissolved in 50% aqueous DMF (3 ml) and the resulting yellow solution stirred overnight at room temperature. The mixture was then concentrated (35°/10$^{-5}$ mmHg) and the yellow residue partitioned between water and chloroform. The water layer was separated, washed with chloroform (2×) and ethyl acetate, and then concentrated to give a yellow oil (134 mg). The crude product was converted to the sodium salt by passage through a column of Amberlite IR 120(Na) to yield 85 mg of material. This material was further purified by gel filtration (Sephadex LH20; water) to give the sodium N-(2-sulfoethyl) succinamide terminated PAMAM 4.0 dendrimer (45 mg). $^{13}$C nmr (D$_2$O): δ33.2, 33.6, 35.5, 39.0, 39.5, 42.8, 43.2, 53.8, 54.1, 54.4, 56.6, 176.5, 176.9, 177.2, 178.9, 179.4.

The corresponding PAMAM 1.0 and PAMAM 3.0 (BRI2785) dendrimers terminated with sodium N-(2-sulfoethyl)succinamide groups were similarly prepared.

$^{13}$C nmr PAMAM 3.0 derivative (D$_2$O): δ33.4, 35.5, 39.0, 39.5, 42.9, 43.2, 53.8, 54.1, 54.3, 56.5, 176.4, 176.9, 177.4, 178.9, 179.4.

$^{13}$C nmr PAMAM 1.0 derivative (D$_2$O): δ34.9, 35.5, 39.5, 42.9, 43.1, 53.7, 54.1, 179.0, 179.1, 179.3.

B Preparation of Sodium N-(2-sulfoethyl)succinamide Terminated Polylysine Dendrimers BHAlyslys$_2$lys$_4$lys$_8$lys$_{16}$ BRI2789

Trifluoroacetic acid (1 ml) was added to a suspension of BHAlyslys$_2$lys$_4$lys$_8$DBL$_{16}$ (36.5 mg; 5.0 μmol) in dry dichloromethane (1 ml) and the resulting solution stirred at room temperature under nitrogen for two hours and then concentrated. The residue was dissolved in dry DMSO (2 ml) and the pH adjusted to 8.5 with triethylamine. A solution of the crude tetrabutylammonium 4-nitrophenyl N-(2-sulfoethyl)succinamate (ca. 0.2 mmol) in DMSO (1 ml) was then added dropwise and the mixture stirred overnight at room temperature. The yellow solution was then concentrated (50°/10$^{-5}$ mmHg) and the yellow residue partitioned between water and chloroform. The aqueous layer was separated, washed with chloroform (3×) and ethyl acetate, and then concentrated to give an oil (99 mg). The crude product was converted to the sodium salt by passage through a column of Amberlite IR 120(Na) to yield 81 mg of material. This material was further purified by gel filtration (Sephadex LH20; water) to give the sodium N-(2-sulfoethyl) succinamide terminated BHAlyslys$_2$lys$_4$lys$_8$lys$_{16}$ dendrimer (39 mg). $^{13}$C nmr (D$_2$O): δ27.0, 32.3, 35.2, 35.6, 35.7, 39.5, 43.5, 54.1, 58.5, 131.5, 132.0, 133.3, 145.1, 177.8, 178.0, 178.4, 178.8, 178.9, 179.2, 179.7, 179.8.

The corresponding BHAlyslys$_2$, BHAlyslys$_2$lys$_4$ (BRI2787) and BHAlyslys$_2$lys$_4$lys$_8$ (BRI2788) terminated with sodium N-(2-sulfoethyl)succinamide groups were similarly prepared.

$^{13}$C nmr BHAlyslys$_2$lys$_4$lys$_8$ derivative (D$_2$O): δ26.9, 32.3, 35.1, 35.3, 35.6, 35.7, 39.5, 43.5, 54.1, 58.5, 131.6, 131.9, 132.2, 132.3, 133.2, 133.3, 145.0, 145.2, 177.2, 177.8, 177.9, 178.0, 178.2, 178.3, 178.6, 178.7, 178.8, 178.9, 179.2, 179.3, 179.7, 179.8.

$^{13}$C nmr BHAlyslys$_2$lys$_4$ derivative (D$_2$O): δ26.9, 32.3, 35.1, 35.4, 35.7, 35.8, 39.5, 43.5, 54.1, 58.5, 61.8, 131.7, 132.0, 132.2, 132.3, 133.2, 133.3, 145.0, 145.1, 177.3, 178.0, 178.3, 178.4, 178.7, 178.9, 179.0, 179.3, 179.7, 179.8.

$^{13}$C nmr BHAlyslys$_2$ derivative (D$_2$O): δ26.9, 27.1, 32.2, 32.3, 34.7, 34.8, 35.1, 35.3, 35.6, 35.7, 39.5, 43.4, 54.1, 58.6, 61.8, 131.7, 131.9, 132.2, 132.3, 133.3, 144.9, 145.0, 177.7, 178.4, 178.8, 179.0, 179.3, 180.0.

EXAMPLE 5

Preparation of Sodium 4-sulfophenylthiourea Terminated Dendrimers

A PAMAM 4.0 BRI2791

Solid sodium 4-sulfophenylisothiocyanate monohydrate (500 mg; 1.96 mmol) was added to a solution of PAMAM 4.0 (300 mg; 0.0582 mmol) in water (10 ml) and the resulting solution heated under nitrogen at 53° for two hours and then cooled. The solution was concentrated and the yellow solid residue purified by gel filtration (Sephadex LH20; water). The pure fractions were combined and freeze dried to give the sodium 4-sulfophenylthiourea terminated PAMAM 4.0 dendrimer as a fluffy white solid (370 mg). $^1$H nmr (D$_2$O): δ2.28; 2.52; 2.69; 3.15; 3.27; 3.60; 7.32 (d, J=9 Hz); 7.72 (d, J=9 Hz). $^{13}$C nmr (D$_2$O): δ36.9; 41.1; 43.1; 48.3; 53.6; 55.8; 129.0; 131.1; 144.4; 178.5; 179.1, 184.4.

The corresponding PAMAM 1.0, PAMAM 2.0 (BRI2790), PAMAM 3.0, and PAMAM 5.0 (BRI2991) dendrimers terminated with 3, 6, 12, and 48 sodium 4-sulfophenylthiourea groups respectively were similarly prepared.

B PAMAM 4.0 (EDA) BRI6045

Solid sodium 4-sulfophenylisothiocyanate monohydrate (130 mg; 0.5 mmol) was added to a solution of PAMAM 4.0 (EDA) (69 mg; 0.01 mmol) in water (4 ml) and the resulting solution heated under nitrogen at 53° for two hours and then cooled. The solution was concentrated and the solid residue purified by gel filtration (Sephadex LH20; water). The pure fractions were combined and freeze dried to give PAMAM 4.0 terminated with 32 sodium 4-sulfophenylthiourea groups as a fluffy white solid (136 mg). $^1$H nmr ($D_2O$): δ2.30; 2.50; 2.70; 3.18; 3.62; 7.35 (d, J=9 Hz); 7.72 (d, J=9 Hz). $^{13}$C nmr ($D_2O$): δ36.8; 41.0; 43.1; 48.4; 53.6; 55.7; 128.9; 131.0; 144.3; 178.5; 179.0; 184.5.

C BHAlyslys$_2$lys$_4$lys$_8$lys$_{16}$ BRI2792

Trifluoroacetic acid (4 ml) was added to a suspension of BHAlyslys$_2$lys$_4$lys$_8$DBL$_{16}$ (0.73 g; 0.1 mmol) in dry dichloromethane (4 ml) under nitrogen. A vigorous evolution of gas was observed for a short time and the resulting solution was stirred at room temperature for two hours and then concentrated. The residual syrup was dissolved in water (5 ml), the solution passed through a column of Amberlite IRA-401 (OH) and the filtrate concentrated to give BHAlyslys$_2$lys$_4$lys$_8$lys$_{16}$ as a viscous oil (0.49 g). The oil was redissolved in water (5 ml) and N,N-dimethyl-N-allylamine buffer (pH 9.5; 3 ml) added. Solid sodium 4-sulfophenylisothiocyanate monohydrate (1.30 g; 5.1 mmol) was then added and the resulting solution heated under nitrogen at 53° for two hours and then cooled. The solution was concentrated and the brownish solid residue purified by gel filtration (Sephadex LH20; water). The pure fractions were combined, passed through a column of Amberlite IR 120(Na) and freeze dried to give the sodium 4-sulfophenylthiourea terminated BHAlyslys$_2$lys$_4$lys$_8$lys$_{16}$ dendrimer as a fluffy white solid (374 mg). $^1$H nmr ($D^2O$): δ1.40; 1.72; 3.08; 3.42; 4.24; 4.60; 7.30; 7.40 (d, J=9 Hz); 7.78 (d, J=9 Hz). $^-$C nmr (D20): 8 27.3; 32.5; 35.9; 43.7; 48.9; 58.6; 63.3; 128.8; 131.0; 143.7; 144.7; 145.1; 177.7; 178.1; 183.8; 185.2.

The corresponding BHAlyslys$_2$lys$_4$lys$_8$, BHAlyslys$_2$lys$_4$lys$_8$lys$_{16}$lys$_{32}$ (BRI2992 and BHAlyslys$_2$lys$_4$lys$_8$lys$_{16}$lys$_{32}$lys$_{64}$ (BRI2993) dendrimers terminated with 16, 64, and 128 sodium 4-sulfophenylthiourea groups respectively were similarly prepared.

EXAMPLE 6

Preparation of Sodium 3,6-disulfonapthylthiourea Terminated Dendrimers

A PAMAM 4.0 BRI2923

Solid sodium 3,6-disulfonapthylisothiocyanate (160 mg; 0.41 mmol) was added to a solution of PAMAM 4.0 (51 mg; 0.01 mmol) in water (3 ml) and the resulting solution heated under nitrogen at 53° for two hours and then cooled. The solution was concentrated and the brown solid residue purified by gel filtration (Sephadex LH20;

water). The pure fractions were combined and concentrated to give the sodium 3,6-disulfonapthylthiourea terminated PAMAM 4.0 dendrimer as a brownish solid (73 mg). $^1$H nmr ($D_2O$): δ2.30; 2.60; 2.74; 3.20; 3.57; 7.75; 7.86; 8.28. $^{13}$C nmr ($D_2O$): δ35.0; 39.9; 43.1; 48.1; 53.8; 56.1; 128.4; 128.6; 129.3; 131.0; 131.3; 136.0; 136.8; 138.2; 145.5; 146.0; 177.2; 177.8; 185.5.

The corresponding PAMAM 2.0 dendrimer terminated with sodium 3,6-disulfonapthylthiourea groups was similarly prepared.

B PAMAM 4.0 (EDA) BRI6046

Solid sodium 3,6-disulfonapthylisothiocyanate (220 mg; 0.57 mmol) was added to a solution of PAMAM 4.0 (EDA) (74 mg; 0.01 mmol) in water (4 ml) and the resulting solution heated under nitrogen at 53° for two hours and then cooled. The solution was concentrated and the brownish solid residue purified by gel filtration (Sephadex LH20; water). The pure fractions were combined and concentrated to give PAMAM 4.0 terminated with 32 sodium 3,6-disulfonapthylthiourea groups as a tan solid (148 mg). $^1$H nmr ($D_2O$): δ2.30; 2.80; 3.20; 3.54; 7.74; 7.85; 8.25. $^{13}$C nmr ($D_2O$): δ36.0; 40.8; 43.1; 48.3; 53.6; 55.9; 128.5; 129.4; 131.0; 131.3; 136.0; 136.8; 138.3; 145.5; 146.0; 178.2; 185.6.

C BHAlyslys$_2$lys$_4$lys$_8$lys$_{16}$ BRI2999

Trifluoroacetic acid (2 ml) was added to a suspension of BHAlyslys$_2$lys$_4$lys$_8$DBL$_{16}$ (73 mg; 0.01 mmol) in dry dichloromethane (2 ml) under nitrogen. A vigorous evolution of gas was observed for a short time and the resulting solution was stirred at room temperature for two hours and then concentrated. The residual syrup was dissolved in water (5 ml), the solution passed through a column of Amberlite IRA-401 (OH) and the filtrate concentrated to give BHAlyslys$_2$lys$_4$lys$_8$lys$_{16}$ as a viscous oil. The oil was redissolved in water (5 ml) and N,N-dimethyl-N-allylamine buffer (pH 9.5; 3 ml) added. Solid sodium 3,6-disulfonapthylisothiocyanate (234 mg; 0.60 mmol) was then added and the resulting solution heated under nitrogen at 53° for two hours and then cooled. The solution was concentrated and the brownish solid residue purified by gel filtration (Sephadex LH20; water). The pure fractions were combined, passed through a column of Amberlite IR 120 (Na) and freeze dried to give BHAlyslys$_2$lys$_4$lys$_8$lys$_{16}$ terminated with 32 sodium 3,6-disulfonapthylthiourea groups as a fluffy off-white solid (119 mg). $^1$H nmr ($D_2O$): δ1.0–2.0; 3.18; 3.43; 4.31; 7.22; 7.80; 7.89; 8.25. $^{13}$C nmr ($D_2O$): δ27.2; 32.4; 35.3; 43.7; 49.0; 58.5; 63.6; 128.4; 129.1; 131.4; 136.1; 136.6; 138.6; 139.0; 145.1; 145.6; 178.4; 184.8; 186.7.

EXAMPLE 7

Preparation of Sodium 4-sulfonapthylthiourea Terminated Dendrimers

PAMAM 4.0 BRI2997

Solid sodium 4-sulfonapthylisothiocyanate (80 mg; 0.5 mmol) was added to a solution of PAMAM 4.0 (51 mg; 0.01 mmol) in water (5 ml) and the mixture heated under nitrogen at 53° for two hours and then cooled. The water was distilled under reduced pressure from the resulting suspension and the off white solid residue purified by gel filtration (Sephadex LH20; water). The pure fractions were combined and freeze dried to give the sodium 4-sulfonapthylthiourea terminated PAMAM 4.0 dendrimer as a fluffy white solid (60 mg). $^1$H nmr ($D_2O$): δ2.20; 2.60; 3.14; 3.48; 7.23; 7.47; 7.56; 7.77; 7.93 (d, J=6 Hz); 8.56 (d, J=6 Hz). $^-$C nmr (D2O): δ35.8; 40.5; 43.1; 48.4; 53.6; 55.9; 127.6; 128.6; 130.3; 131.9; 132.5; 133.5; 134.7; 140.5; 142.7; 177.8; 178.0; 185.4.

EXAMPLE 8

Preparation of Sodium 3,5-disulfophenylthiourea Terminated Dendrimers

PAMAM 4.0 BRI6039

Solid sodium 3,5-disulfophenylisothiocyanate (110 mg; 0.32 mmol) was added to a solution of PAMAM 4.0 (63 mg; 0.012 mmol) in water (3 ml) and the resulting solution heated under nitrogen at 53° for two hours and then cooled. The solution was concentrated and the brownish solid residue purified by gel filtration (Sephadex G25; water). The pure fractions were combined and concentrated to give PAMAM 4.0 terminated with 24 sodium 3,5-disulfophenylthiourea groups as an off-white solid (110 mg). $^1$H nmr (D$_2$O): δ2.53; 3.08; 3.36; 3.66; 7.90; 7.95. $^{13}$C nmr (D$_2$O): δ34.8; 41.0; 43.1; 48.0; 53.7; 56.2; 124.1; 128.6; 143.5; 148.8; 177.6; 185.0.

EXAMPLE 9

Preparation of sodium 3,6,8-trisulfonaphthylthiourea Terminated Dendrimers PAMAM 4.0 BRI2998

Solid sodium 3,6,8-trisulfonaphthylisothiocyanate (250 mg; 0.5 mmol) was added to a solution of PAMAM 4.0 (51 mg; 0.01 mmol) and N,N-dimethyl-N-allylamine buffer (pH 9.5; 1 ml) in water (2 ml) and the mixture heated under nitrogen at 53° for two hours and then cooled. The mixture was concentrated under reduced pressure to give an orange solid. The residual solid was dissolved in water (2 ml) and passed through a short column of Amberlite IR-120(Na). The filtrate was then concentrated and the residue purified by gel filtration (Sephadex LH20; water). The pure fractions were combined and freeze dried to give the sodium 3,6,8-trisulfonaphthylthiourea terminated PAMAM 4.0 dendrimer as an off-white solid (102 mg). $^1$H nmr (D$_2$O): δ2.65; 3.02; 3.30; 3.66; 8.05; 8.42; 8.59; 8.67. $^{13}$C nmr (D$_2$O): δ33.2; 38.7; 43.2; 43.7; 47.8; 54.0; 54.3; 56.7; 131.0; 131.3; 131.9; 135.9; 138.0; 139.6; 143.8; 144.1; 145.6; 176.2; 176.5; 186.0.

EXAMPLE 10

Preparation of Sodium 4-(sulfomethyl)benzamide Terminated Dendrimers PAMAM 4.0 BRI6040

Solid 4-nitrophenyl 4-(chloromethyl)benzoate (200 mg; 0.68 mmol) was added to a stirred solution of PAMAM 4.0 (70 mg; 0.014 mmol) in dry DMSO (4 ml) and the resulting yellow solution stirred at room temperature for two hours. The solution was then concentrated (10$^{-4}$ mmHg; 40°) and the residue extracted with a mixture of water and dichloromethane (1:1). The remaining solid material was dissolved in DMSO (5 ml) and a solution of sodium sulfite (130 mg; 1 mmol) in water (3 ml) added. The slightly cloudy mixture that resulted was left to stand for four days, after which time the addition of more water (2 ml) resulted in the formation of a clear homogeneous yellow solution. The solution was then concentrated, first at 25 mmHg and 40° then at 10$^{-4}$ mmHg and 50° to give the crude product. The crude product was purified by gel filtration (Sephadex G25; water) to give PAMAM 4.0 terminated with 24 sodium 4-(sulfomethyl) benzamide groups (24 mg). $^1$H nmr (D$_2$O): δ2.25; 2.66; 3.08; 3.20; 3.33; 3.38; 4.01; 7.40 (br d); 7.62 (br d). $^{13}$C nmr (D$_2$O): δ36.7; 40.9; 43.0; 43.6; 53.5; 55.5; 61.0; 131.6; 135.0; 137.2; 140.4; 174.5; 178.6; 179.2.

EXAMPLE 11

Preparation of 4-sulfobenzamide Terminated Dendrimers PAMAM 4.0 (EDA) BRI6116

Solid potassium N-hydroxysuccinimidyl 4-sulfobenzoate (100 mg; 0.3 mmol) was added to a solution of PAMAM 4.0 (EDA) (35 mg; 0.005 mmol) in 0.1 M pH 8.5 borate buffer (5 ml) and the solution stirred at room temperature for two hours. The resulting milky solution at this stage had a pH of 4.5. 1 M Sodium carbonate solution (1 ml) was then added to give a clear solution which was concentrated to give the crude product as a white solid. The crude product was purified by gel filtration (Sephadex G25; water) to give PAMAM 4.0 (EDA) terminated with 32 sodium 4-sulfobenzamide groups (47 mg). $^1$H nmr (D$_2$O): δ2.25; 2.42; 2.63; 3.05; 3.18; 3.31; 3.38; 7.72 (d, J=8 Hz); 7.78 (d, J=8 Hz). $^{13}$C nmr (D$_2$O): δ36.0; 40.4; 43.0; 43.7; 53.7; 55.8; 130.2; 132.2; 140.4; 150.1; 173.6; 178.0; 178.5.

EXAMPLE 12

Preparation of Sodium N-(4-sulfophenyl) propanamide Terminated Dendrimers PAMAM 4.0 (EDA) BRI6117

Solid sodium N-(4-sulfophenyl)acrylamide (250 mg; 1 mmol) and solid sodium carbonate (106 mg; 1 mmol) were added successively to a stirred solution of PAMAM 4.0 (EDA) (78 mg; 0.011 mmol) in water (4 ml). The resulting solution was stirred under nitrogen for four days and then freeze dried to give a fluffy white solid. The crude product was purified by gel filtration (Sephadex LH20; water to give PAMAM 4.0 (EDA) terminated with 64 sodium N-(4-sulfophenyl)propanamide groups (206 mg). $^{13}$C nmr showed a faint trace of what was taken to be mono alkylated terminal amino groups. $^1$H nmr (D$_2$O): δ2.10; 2.48; 2.58; 2.79; 3.20; 7.42 (d, J=7 Hz); 7.65 (d, J=7 Hz). $^{13}$C nmr (D$_2$O): δ36.5; 37.9; 41.1; 53.4; 55.6; 124.8; 130.9; 143.0; 144.2; 177.4; 178.5.

EXAMPLE 13

Preparation of Sodium 4-sulfophenylurea Terminated Dendrimers PAMAM 4.0 (EDA) BRI6115

A solution of sodium sulfanilic acid (195 mg; 1 mmol) in dry DMSO (3 ml) was added dropwise to a solution of N,N'-disuccinimidyl carbonate (530 mg; 2 mmol) in dry DMSO (4 ml) and the resulting brownish solution stirred at room temperature for 20 hours. A solution of PAMAM 4.0 (EDA) (75 mg; 0.011 mmol) in dry DMSO (1 ml) added and the solution stirred for a further 18 hours. The solution was then concentrated under high vacuum (10$^{-5}$ mmHg; 35°) to give a yellowish semi-solid. The crude product was dissolved in DMSO (4 ml) and the solution added to 200 ml of well stirred ethyl acetate. The precipitated white solid was collected by filtration and washed with ethyl acetate (2×) and ether (2×), then dried to give a white powder (275 mg). This material was further purified by gel filtration (Sephadex LH20; water) to give PAMAM 4.0 (EDA) terminated with 32 sodium 4-sulfophenylurea groups (106 mg). $^1$H nmr (D$_2$O): δ2.31; 2.55; 2.75; 3.19; 7.32 (d, J=9 Hz); 7.63 (d, J=9 Hz). $^{13}$C nmr (D$_2$O): δ36.3; 40.7; 43.3; 43.8; 53.7; 55.7; 123.3; 130.9; 140.9; 146.0; 161.4; 178.2; 178.6.

EXAMPLE 14

Preparation of N,N,N-trimethylglycinamide Chloride Terminated Dendrimers BHAlyslys$_2$lys$_4$lys$_8$lys$_{16}$ BRI2922

Trifluoroacetic acid (4 ml) was added to a suspension of BHAlyslys$_2$lys$_4$lys$_8$DBL$_{16}$ (220 mg; 30 μmol) in dry dichloromethane (2 ml) and the resulting solution stirred at room temperature under nitrogen for two hours and then concentrated. The residue was dissolved in dry DMSO (5 ml) and the pH adjusted to 8.5 with triethylamine. Solid 4-nitrophenyl N,N,N-trimethylglycinate chloride (0.50 g; 1.8 mmol) was then added and the mixture stirred overnight at room temperature. The cloudy solution was then concentrated (50°/10$^{-5}$ mmHg) and the residue partitioned between water and dichloromethane. The aqueous layer was separated, washed with dichloromethane (3×) and ethyl acetate, and then concentrated to give an oil (1.128 g). The crude product was purified by gel filtration (Sephadex LH20; water) to give the N,N,N-trimethylglycinamide terminated BHAlyslys$_2$lys$_4$lys$_8$lys$_{16}$ dendrimer (116 mg). $^{13}$C nmr (D2O): δ25.5, 30.5, 30.8, 33.4, 42.1, 56.5, 57.1, 67.5, 68.1, 166.7, 167.0, 167.1, 176.0, 176.2.

EXAMPLE 15

Preparation of 4-Trimethylammoniumbenzamide Terminated Dendrimers
PAMAM 4.0 BRI6043

1,1'-Carbonyldiimidazole (85 mg; 0.52 mmol) was added to a solution of 4-trimethylammoniumbenzoic acid iodide (154 mg; 0.5 mmol) in dry DMF (4 ml) and the mixture stirred at room temperature under argon for two hours. During this time a white solid separated from the solution. A solution of PAMAM 4.0 (58 mg; 0.011 mmol) in dry DMF (2 ml) was then added and the mixture stirred overnight at room temperature. After this time most of the precipitate had dissolved and a ninhydrin test of the solution was negative. The mixture was concentrated ($10^{-4}$ mmHg; 30°) to give a white solid residue. The crude product was purified by gel filtration (Sephadex LH20; 10% AcOH) to give PAMAM 4.0 terminated with 24 4-trimethylammoniumbenzamide groups as the acetic acid salt (89 mg). $^1$H nmr (D2O): δ1.96; 2.65–2.85; 3.25–3.55; 3.64; 7.92. $^{13}$C nmr (D$_2$O): δ25.8; 33.1; 33.5; 38.7; 43.1; 43.5; 53.5; 54.1; 56.4; 61.2; 124.8; 133.6; 139.9; 153.2; 173.2; 176.3; 176.8; 182.6.

The corresponding PAMAM 2.0 dendrimer terminated with 6 4-trimethylammonium benzamide groups was similarly prepared.

EXAMPLE 16

Preparation of 4-(Trimethylammoniummethyl) benzamide Terminated Dendrimers
PAMAM 4.0 BRI6044

Solid 4-nitrophenyl 4-(chloromethyl)benzoate (150 mg; 0.5 mmol) was added to a stirred solution of PAMAM 4.0 (52 mg; 0.01 mmol) in dry DMSO (3 ml). The resulting yellow solution was stirred at room temperature for 20 hours, when a ninhydrin test was negative (pH ca.8.5). The solution was then concentrated ($10^{-5}$ mmHg; 40°) and the residue shaken with a mixture of water and dichloromethane (1:1). The insoluble gel-like material was collected by filtration, washed with water (2×) and dichloromethane (2×), and then air dried. The crude 4-(chloromethyl)benzamide terminated dendrimer was dissolved in 25% aq. trimethylamine (20 ml) and the yellow solution left to stand overnight. The solution was then concentrated, the residue dissolved in water (5 ml) and the solution passed through a column of Amberlite IRA-401 (OH). The colourless filtrate was concentrated to give a viscous oil which was purified by gel filtration (Sephadex G10; 10% AcOH) to give PAMAM 4.0 terminated with 24 4-(trimethylammoniummethyl) benzamide groups (90 mg). $^1$H nmr (D$_2$O): δ1.88; 2.65–2.80; 2.98; 3.10–3.60; 7.52 (br d, J=9 Hz); 7.72 (br d, J=9 Hz). $^{13}$C nmr (D$_2$O): δ26.6; 33.4; 38.8; 43.2; 43.5; 53.6; 53.6; 54.1; 56.8; 62.8; 73.0; 132.1; 135.3; 137.5; 140.0; 176.4; 176.9; 183.6.

EXAMPLE 17

Preparation of N-(2-Acetoxyethyl)-N,N-(dimethylammonium)methyl-carboxamide Terminated Dendrimers
PAMAM 4.0

Solid 1,1'-carbonyldiimidazole (85 mg; 0.52 mmol) was added to a solution of N-(2-acetoxyethyl)-N-(carboxymethyl)-N,N-dimethylammonium bromide (135 mg; 0.5 mmol) in dry DMF (3 ml) and the resulting solution stirred under nitrogen for two hours. A solution of PAMAM 4.0 (60 mg; 0.012 mmol) in DMF (2 ml) was then added, which caused the immediate formation of a flocculant precipitate which slowly redissolved. The mixture was stirred for two days and then concentrated ($10^{-4}$ mmHg; 40°) to give a viscous oil. The crude product was purified by gel filtration (Sephadex G10; 10% AcOH) to give PAMAM 4.0 terminated with 24 N-(2-Acetoxyethyl)-N,N-(dimethylammonium)methylcarboxamide groups (64 mg). $^1$H nmr (D$_2$O): δ1.93; 2.05; 2.70; 3.10–3.60; 3.28; 3.93 (m); 4.14; 4.48 (m). $^{13}$C nmr (D$_2$O): δ24.6; 26.2; 33.2; 38.7; 42.8; 42.9; 53.9; 57.4; 62.6; 67.3; 67.5; 168.9; 176.4; 176.8; 177.3; 183.2.

EXAMPLE 18

Preparation of Guanidino Terminated Dendrimers
PAMAM 4.0 BRI6042

A solution of PAMAM 4.0 (63 mg; 0.012 mmol) and methylthiopseudourea sulfate (170 mg; 0.61 mmol) in water (5 ml) (pH 10.5) was heated under nitrogen at 80° for two hours. The solution was then concentrated and the residue purified by gel filtration (Sephadex G10; 10% AcOH) to give PAMAM 4.0 terminated with 24 guanidino groups as the acetate salt (107 mg). $^1$H nmr (D$_2$O): δ2.00; 2.80 (br t); 3.09 (br t); 3.32; 3.45 (br t); 3.60 (br t). $^{13}$C nmr (D$_2$O): δ25.2; 33.2; 33.4; 38.7; 41.2; 42.6; 43.4; 44.7; 53.5; 54.0; 56.3; 176.5; 176.7; 176.9; 181.6.

The corresponding PAMAM 2.0 dendrimer terminated with 6 guanidino groups was similarly prepared.

EXAMPLE 19

Preparation of 4-([1,4,8,11-tetraazacyclotetradecane] methyl)benzamide Terminated Dendrimers
PAMAM 4.0 BRI6041

A solution of 1-(4-carboxyphenyl)methyl-1,4,8,11-tetraazacyclotetradecane tetra hydrochloride (120 mg; 0.25 mmol), N-hydroxysuccinimide (60 mg; 0.52 mmol) and 1-(3-dimethylaminopropyl)-3-ethylcarbodiimide hydrochloride (250 mg; 1.3 mmol) in pH 7 phosphate buffer (10 ml) was allowed to stand a room temperature for one hour and then a solution of PAMAM 4.0 (32 mg; 0.006 mmol) in pH 7 phosphate buffer (10 ml) added. The mixture was allowed to stand for two days and then concentrated. The residue was purified by gel filtration (Sephadex LH20; 10% AcOH) to give PAMAM 4.0 terminated with ca. 12 4-([1,4,8,11-tetraazacyclotetradecane]methyl)-benzamide groups as determined by $^1$H and $^{13}$C nmr (80 mg). The product was then dissolved in water and passed through a column of Amberlite IRA-401 (Cl) resin and then concentrated. The residue was dissolved in water (1 ml), concentrated HCl (1 ml) added, and the solution diluted with ethanol (30 ml) to precipitate a white solid. The solid was collected by filtration (68 mg). Once again $^1$H and $^{13}$C nmr showed ca. 50% functionalisation of the terminal amino groups. $^1$H nmr (D$_2$O): δ2.17; 2.36; 2.50; 2.78; 2.85; 3.25; 3.40; 3.50; 3.60; 3.62; 4.49; 7.63 (br d); 7.78 (br d). $^{13}$C nmr (D$_2$O): δ22.7; 23.1; 33.2; 38.8; 39.9; 40.2; 40.3; 41.0; 41.2; 42.0; 42.9; 43.2; 43.6; 45.5; 46.1; 49.1; 52.2; 53.9; 54.3; 56.6; 62.7; 132.5; 135.7; 137.1; 139.7; 174.3; 176.2; 176.3; 176.7; 177.0; 178.2; 178.5.

EXAMPLE 20

Preparation of 4-Carboxy-3-hydroxybenzylamine Terminated Dendrimers
PAMAM 4.0 (EDA) BRI6119

Sodium cyanoborohydride (32 mg; 0.5 mmol) was added to a mixture of PAMAM 4.0 (EDA) (69 mg; 0.01 mmol), 4-formyl-2-hydroxybenzoic acid (83 mg; 0.5 mmol), and sodium hydrogen carbonate (42 mg; 0.5 mmol) in water (4 ml). The inhomogeneous orange mixture was stirred for four hours at room temperature, during which time it became homogeneous. The orange solution was then concentrated and the residue purified by gel filtration (Sephadex LH20; water) to give PAMAM 4.0 (EDA) terminated with ca. 32 4-carboxy-3-hydroxybenzylamine groups (91 mg). $^1$H and $^{13}$C nmr (D$_2$O) shows mostly mono alkylation but with some signs of dialkylation of the terminal amino groups, both spectra show broad peaks. $^{13}$C nmr (D$_2$O): δ37.0; 41.1; 50.9; 53.4; 55.5; 55.8; 61.5; 120.9; 122.2; 122.4; 132.3; 132.7; 135.0; 135.8; 163.5; 163.7; 169.0; 178.6; 179.3. $^1$H nmr (D$_2$O): δ2.20; 2.35; 2.60; 3.15; 3.30; 3.55; 4.25; 6.68; 7.12; 7.55.

EXAMPLE 21

Preparation of 4-Carboxyphenylamide Terminated Dendrimers
PAMAM 4.0 (EDA)

Solid 4-carboxyphenylisothiocyanate (86 mg; 0.48 mmol) was added to a solution of PAMAM 4.0 (EDA) (69 mg; 0.01 mmol) in water (20 ml). The pH of the resulting cloudy solution was adjusted to 9 with saturated NaHCO$_3$ solution and left to stir at room temperature for 24 hours. The reaction mixture was then filtered and the filtrate concentrated to give a white solid residue, which was purified by gel filtration (Sephadex LH20; water) and then freeze dried to give the product as a white fluffy solid (68 mg).

EXAMPLE 22

Preparation of 3,5-Dicarboxyphenylamide Terminated Dendrimers
PAMAM 4.0 (EDA)

Solid 3,5-dicarboxyphenylisothiocyanate (112 mg; 0.5 mmol) was added to a solution of PAMAM 4.0 (EDA) (70 mg; 0.01 mmol) in water (5 ml). The pH of the resulting cloudy solution was adjusted to 10 with 1M Na$_2$CO$_3$ solution and heated under nitrogen at 53° for 2 hours. The reaction mixture was then filtered and the filtrate concentrated to give a brownish solid residue, which was purified by gel filtration (Sephadex LH20; water) and then freeze dried to give the product as a pale brown solid (112 mg).

EXAMPLE 23

Preparation of Sodium 4-Phosphonooxyphenylthiourea Terminated Dendrimers
PAMAM 4.0 (EDA)

Solid sodium 4-phosphonooxyphenylisothiocyanate (251 mg) was added to a solution of PAMAM 4.0 (EDA) (69 mg; 0.01 mmol) in water (20 ml). The resulting solution (pH 9) was stirred for 24 hours at room temperature under nitrogen. The reaction mixture was then concentrated to give a white solid residue, which was purified by gel filtration (Sephadex LH20; water) and then freeze dried to give the product as a fluffy white solid (86 mg).

EXAMPLE 24

Preparation of Sodium 4-(Phosphonomethyl) phenylthiourea Terminated Dendrimers
PAMAM 4.0 (EDA)

Solid sodium 4-(phosphonomethyl)phenylisothiocyanate (97 mg) was added to a solution of PAMAM 4.0 (EDA) (69 mg; 0.01 mmol) in water (30 ml). The resulting solution was stirred for 3 days at room temperature under nitrogen, maintaining the pH at 8 with periodic addition of saturated NaHCO$_3$ solution. The reaction mixture was then concentrated to give a white solid residue, which was purified by gel filtration (Sephadex LH20; water) and then freeze dried to give the product as a fluffy white solid (102 mg).

EXAMPLE 25

Preparation of Sodium Ethyl 4-(Phosphonomethyl) phenylthiourea Terminated Dendrimers
PAMAM 4.0 (EDA)

Solid sodium ethyl 4-(phosphonomethyl) phenylisothiocyanate (109 mg) was added to a solution of PAMAM 4.0 (EDA) (69 mg; 0.01 mmol) in DMF (30 ml). The resulting solution was stirred for 17 hours at room temperature under nitrogen, maintaining the pH at 8 with periodic addition of saturated NaHCO$_3$ solution. The reaction mixture was then concentrated to give a white solid residue, which was purified by gel filtration (Sephadex LH20; water) and then freeze dried to give the product as a fluffy white solid (30 mg).

EXAMPLE 26

Preparation of Sodium 4-Sulfophenylthiourea Terminated Polylysines

Solid sodium 4-sulfophenylisothiocyanate monohydrate (2.55 g; 10 mmol) was added to a solution of poly-L-lysine (15–30K) (Sigma Chemical Company) (1.0 g) in a mixture of water (20 ml) and N,N-dimethyl-N-allylamine buffer (pH 9.5; 15 ml). The resulting mixture was heated under nitrogen at 53° C. for 3 hours, when a ninhydrin test was negative. The cooled mixture was filtered and the filtrate concentrated to give a grey solid residue. The solid residue was redissolved in water and passed through a column of Amberlite IR 120(Na) and then concentrated. The crude product was purified by gel filtration (Sephadex LH20; water) and freeze dried to give sodium 4-sulfophenylthiourea terminated poly-L-lysine BRI2995 as a white fluffy solid (1.25 g).

Similarly prepared were sodium 4-sulfophenylthiourea terminated polylysines of molecular weight fraction 1–4K BRI2994, 4–15K BRI2967, 150–300K BRI2996.

EXAMPLE 27

Preparation of Sodium 3,6-Disulfonapthylthiourea Terminated Polylysines

Solid sodium 3,6-Disulfonapthylisothiocyanate (200 mg; 0.51 mmol) was added to a solution of poly-L-lysine (15–30K) (50 mg) in a mixture of water (2 ml) and N,N-dimethyl-N-allylamine buffer (pH 9.5; 2 ml). The resulting mixture was heated under nitrogen at 53° C. for 3 hours, when a ninhydrin test was negative. The cooled mixture was filtered and the filtrate concentrated to give a brownish solid residue. The solid residue was redissolved in water and passed through a column of Amberlite IR 120(Na) and then concentrated. The crude product was purified by gel filtration (Sephadex LH20; water) and freeze dried to give sodium 3,6-disulfonaphthylthiourea terminated poly-L-lysine BRI6047 as a white fluffy solid (87 mg).

EXAMPLE 28

Preparation of C$_n$-alkyl Linked 2-thiosialoside Terminated Dendrimers and Linear Polymers Methyl [(8-octanoic acid N-hydroxysuccinimide ester) 5-acetamido-4,7,8,9-tetra-O-acetyl-3,5-dideoxy-2-thio-D- glycero-α-D-galacto-2-nonulopyranosid]onate was prepared by the following procedure.

To a solution of methyl 5-acetamido-4,7,8,9-tetra-O-acetyl-2-S-acetyl-3,5-dideoxy-2-thio-D-glycero-α-D-galacto-2-nonulopyranosonate (Hasegawa et al, 1986) (100 mg.) in dry dimethylformamide (1 ml) was added 8-bromooctanoic acid (41 mg.) and diethylamine (280 mg.) and the solution stirred at 20° C. for 17 hours. Solvent was removed under vacuum and the residue partitioned between ethyl acetate and ice cold 5% hydrochloric acid. The organic layer was washed with water, dried over sodium sulphate, and evaporated to give a residue (130 mg.).This was dissolved in ethyl acetate (5 ml.) and N-hydroxysuccinimide (26 mg.) and dicyclohexylcarbodiimide (46 mg.) were added. The mixture was stirred at 20° C. for 17 hours then the white precipitate was filtered off. The filtrate was concentrated and purified by flash chromatography on silica gel eluting with ethyl acetate. Fractions containing product were combined and evaporated to give a white foam 97 mg. 71%.
Similarly were prepared:
Methyl [(11-undecanoic acid N-hydroxysuccinimide ester) 5-acetamido-4,7,8,9-tetra-O-acetyl-3,5-dideoxy-2-thio-D-glycero-α-D-galacto-2-nonulopyranosid]onate.
Methyl [(acetic acid N-hydroxysuccinimide ester) 5-acetamido-4,7,8,9-tetra-O-acetyl-3,5-dideoxy-2-thio-D-glycero-α-D-galacto-2-nonulopyranosid]onate.
Methyl [(4-butanoic acid N-hydroxysuccinimide ester) 5-acetamido-4,7,8,9-tetra-O-acetyl-3,5-dideoxy-2-thio-D-glycero-α-D-galacto-2-nonulopyranosid]onate.
Methyl [(4-methylbenzoic acid N-hydroxysuccinimide ester) 5-acetamido-4,7,8,9-tetra-O-acetyl-3,5-dideoxy-2-thio-D-glycero-α-D-galacto-2-nonulopyranosid]onate.
A PAMAM [EDA] 4.0 [(8-octanamido)-5-acetamido-3,5-dideoxy-2-thio-D-glycero-α-D-galacto-2-nonulopyranosidoic acid]$_{32}$ BRI 6112

To a solution of the PAMAM [EDA] 4.0 (50 mg.) in dry dimethyl sulphoxide (4 ml.) under an inert atmosphere was added methyl [(8-octanoic acid N-hydroxysuccinimide ester) 5-acetamido-4,7,8,9-tetra-O-acetyl-3,5-dideoxy-2-thio-D-glycero-α-D-galacto-2-nonulopyranosid]onate (300 mg.) and the solution stirred for 60 hours at 20° C. The solvent was removed under vacuum and the residue was dissolved in methanol (2 ml.). This solution was subjected to size exclusion chromatography on Sephadex LH20 eluting with methanol. On evaporation of solvent, the product, PAMAM [EDA] 4.0 [methyl[(8-octanamido) 5-acetamido-4,7,8,9-tetra-O-acetyl-3,5-dideoxy-2-thio-D-glycero-α-D-galacto-2-nonulopyranosid]onate]$_{32}$ was obtained as a white powder. 182 mg. 93%

This was converted to the free sialoside by the following method:

To a solution of PAMAM [EDA] 4.0 [methyl[(8-octanamido) 5-acetamido-4,7,8,9-tetra-O-acetyl-3,5-dideoxy-2-thio-D-glycero-α-D-galacto-2-nonulopyranosid]onate]$_{32}$ (182 mg.) in dry methanol (3 ml.) under argon at 20° C. was added a freshly prepared 0.19M solution of sodium methoxide in methanol (7 ml.) and the mixture stirred for 2.5 hours. The solvent was evaporated and the residue dissolved in water (10 ml.) and stirred for 3 hours. This solution was subjected to size exclusion chromatography on Sephadex LH20 eluting with water. On lyophilisation, the product, PAMAM [EDA] 4.0 [(8-octanamido)-5-acetamido-3,5-dideoxy-2-thio-D-glycero-α-D-galacto-2-nonulopyranosidoic acid]$_{32}$ was obtained as a pale lemon powder 110 mg. 77%

By a similar procedure were prepared:
PAMAM [EDA] 4.0 [(11-undecanamido)-5-acetamido-3,5-dideoxy-2-thio-D-glycero-α-D-galacto-2-nonulopyranosidoic acid]$_{32}$ BRI 6147
PAMAM [EDA] 4.0 [(acetamido)-5-acetamido-3,5-dideoxy-2-thio-D-glycero-α-D-galacto-2-nonulopyranosidoic acid]$_{32}$ BRI 6121
PAMAM [EDA] 4.0 [(4-methylbenzamido)-5-acetamido-3,5-dideoxy-2-thio-D-glycero-α-D-galacto-2-nonulopyranosidoic acid]$_{32}$ BRI 6120
B BHA lyslys$_2$lys$_4$lys$_8$lys$_{16}$ [(8-octanamido)-5-acetamido-3,5-dideoxy-2-thio-D-glycero-α-D-galacto-2-nonulopyranosidoic acid]$_{32}$ BRI 6169

A solution of BHA lyslys$_2$lys$_4$lys$_8$lys$_{16}$ (t-Boc)$_{32}$ (20.3 mg.) in a mixture of trifluoroacetic acid (2 ml.) and dichloromethane (2 ml.) was stirred at 20° C. for 2 hours then solvent was removed under vacuum. The residue was dissolved in dry dimethyl sulphoxide (1 ml.) and di-isopropylethylamine (25 mg.) and methyl [(8-octanoic acid N-hydroxysuccinimide ester) 5-acetamido-4,7,8,9-tetra-O-acetyl-3,5-dideoxy-2-thio-D-glycero-α-D-galacto-2-nonulopyranosid]onate (78 mg.) were added. The mixture was stirred under argon at 20° C. for 60 hours then solvent was removed under vacuum. The residue was dissolved in a freshly prepared 0.1M solution of sodium methoxide in methanol (2.5 ml.) and the mixture stirred for 3 hours under argon at 20° C. The solvent was evaporated and the residue dissolved in water (1 ml.) and stirred for 17 hours . This solution was subjected to size exclusion chromatography on Sephadex LH20 eluting with water. After lyophilisation ,the product, BHA lyslys$_2$lys$_4$lys$_8$lys$_{16}$ [(8-octanamido)-5-acetamido-3,5-dideoxy-2-thio-D-glycero-α-D-galacto-2-nonulopyranosidoic acid]$_{32}$ was obtained as a white powder 44 mg. 86%.

C Poly-L-lysyl [(8-octanamido)-5-acetamido-3,5-dideoxy-2-thio-D-glycero-α-D-galacto-2-nonulopyranosidoic acid]$_n$ BRI 6150

To a solution of poly-L-lysine.HBr MW 150–300 Kd (22 mg.) in dry dimethyl sulphoxide (1 ml.) were added di-isopropylethylamine (15 mg.) and methyl [(8-octanoic acid N-hydroxysuccinimide ester) 5-acetamido-4,7,8,9-tetra-O-acetyl-3,5-dideoxy-2-thio-D-glycero-α-D-galacto-2-nonulopyranosid]onate (90 mg.). The mixture was stirred under argon at 20° C. for 60 hours then solvent was removed under vacuum. The residue was dissolved in a freshly prepared 0.5M solution of sodium methoxide in methanol (4 ml.) and the mixture stirred for 48 hours under argon at 20° C. The solvent was evaporated and the residue dissolved in water (1.5 ml.) and stirred for 24 hours . This solution was subjected to size exclusion chromatography on Sephadex LH20 eluting with water. After lyophilisation, the product, polylysyl [(8-octanamido)-5-acetamido-3,5-dideoxy-2-thio-D-glycero-α-D-galacto-2-nonulopyranosidoic acid]$_n$ was obtained as a white powder 49 mg. 94%.

EXAMPLE 29

Preparation of Dendritic Sialosides Modified in the 4-position of Sialic Acid

Methyl 4-azido-5-acetamido-7,8,9-tri-O-acetyl-2-S-acetyl-3,4,5-trideoxy-2-thio-D-glycero-α-D-galacto-2-nonulopyranosonate was prepared by the following procedure. To a solution of methyl 4-azido-5-acetamido-7,8,9-tri-O-acetyl-2-chloro-3,4,5-trideoxy-D-glycero-β-D-galacto-2-nonulopyranosonate (Sabesan, 1994) (5 g.) in dry dichloromethane (150 ml.) was added finely powdered potassium thiolacetate (5.8 g.) and the suspension stirred vigorously at 20° C. for 48 hours. The mixture was filtered and evaporated to give a light brown foam (5.2 g.). The required product was isolated by preparative reversed phase HPLC [C$_{18}$, 30% acetonitrile/water] as a white foam 3.9 g. 72%.

Methyl [(8-octanoic acid N-hydroxysuccinimide ester) 4-azido-5-acetamido-7,8,9-tri-O-acetyl-3,4,5-trideoxy-2-thio-D-glycero-α-D-galacto-2-nonulopyranosid]onate was prepared by the following procedure.

To a solution of methyl 4-azido-5-acetamido-7,8,9-tri-O-acetyl-2-S-acetyl-3,4,5-trideoxy-2-thio-D-glycero-α-D-galacto-2-nonulopyranosonate (300 mg.) in dry dimethylformamide (3.5 ml.) was added 8-bromooctanoic acid (155 mg.) and diethylamine (1.26 ml.) and the solution stirred at 20° C. for 17 hours. Solvent was removed under vacuum and the residue partitioned between ethyl acetate and ice cold 10% hydrochloric acid. The organic layer was washed with water, dried over sodium sulphate, and evaporated to give a yellow foam (385 mg.). This was dissolved in ethyl acetate (20 ml.) and N-hydroxysuccinimide (95 mg.) and dicyclohexylcarbodiimide (175 mg.) were added. The mixture was stirred at 20° C. for 17 hours then the white precipitate was filtered off. The filtrate was concentrated and purified by preparative reversed phase HPLC [$C_{18}$, 30% acetonitrile/water] to give a white foam 340 mg. 83%.

A PAMAM [EDA] 4.0 [(8-octanamido)-4-azido-5-acetamido-3,4,5-trideoxy-2-thio-D-glycero-α-D-galacto-2-nonulopyranosidoic acid]$_{32}$ BRI 6146

To a solution of the PAMAM [EDA] 4.0 (72 mg.) in dry dimethyl sulphoxide (5 ml.) under an inert atmosphere was added methyl [(8-octanoic acid N-hydroxysuccinimide ester) 4-azido-5-acetamido-7,8,9-tri-O-acetyl-3,4,5-trideoxy-2-thio-D-glycero-α-D-galacto-2-nonulopyranosid]onate (318 mg) and the solution stirred for 60 hours at 20° C. The solvent was removed under vacuum and the residue was dissolved in methanol (2 ml.). This solution was subjected to size exclusion chromatography on Sephadex LH20 eluting with methanol. On evaporation of solvent, the product, PAMAM [EDA] 4.0 [methyl[(8-octanamido)4-azido-5-acetamido-7,8,9-tri-O-acetyl-3,4,5-trideoxy-2-thio-D-glycero-α-D-galacto-2-nonulopyranosid]onate]$_{32}$ was obtained as a white foam. 225 mg. 81%

The free sialoside was obtained by the following method:
To a solution of PAMAM [EDA] 4.0 [methyl[(8-octanamido) 4-azido-5-acetamido-7,8,9-tri-O-acetyl-3,4,5-trideoxy-2-thio-D-glycero-α-D-galacto-2-nonulopyranosid]onate]$_{32}$ (215 mg.) in dry methanol (1 ml.) under argon at 20° C. was added a freshly prepared 1M solution of sodium methoxide in methanol (1 ml.) and the mixture stirred for 3 hours. The solvent was evaporated and the residue dissolved in water (2 ml.) and stirred for 17 hours. This solution was subjected to size exclusion chromatography on Sephadex LH20 eluting with water. On lyophilisation, the product, PAMAM [EDA] 4.0 [(8-octanamido)-4-azido-5-acetamido-3,4,5 -trideoxy-2-thio-D-glycero-α-D-galacto-2-nonulopyranosidoic acid]$_{32}$ was obtained as a fluffy white powder 160 mg. 90%

B PAMAM [EDA] 4.0 [(8-octanamido)-4-amino-5-acetamido-3,4,5-trideoxy-2-thio-D-glycero-α-D-galacto-2-nonulopyranosidoic acid]$_{32}$ BRI 6149

A slow steam of hydrogen sulphide gas was passed into a solution of PAMAM [EDA] 4.0 [(8-octanamido)-4-azido-5-acetamido-3,4,5-trideoxy-2-thio-D-glycero-α-D-galacto-2-nonulopyranosidoic acid]$_{32}$ (25 mg.) in a mixture of pyridine (40 ml.) and water (20 ml.) at 20° C. for 5 days. The solution was then bubbled with nitrogen for 2 hours to remove excess hydrogen sulphide. The solution was evaporated to dryness and the residue taken up in water (5 ml) and filtered through a 0.45 μm. membrane filter to remove sulphur. On lyophilisation, the product, PAMAM [EDA] 4.0 [(8-octanamido)-4-amino-S-acetamido-3,4,5-trideoxy-2-thio-D-glycero-α-D-galacto-2-nonulopyranosidoic acid]$_{32}$ was obtained as a fluffy white powder 23 mg. 96%

EXAMPLE 30

Preparation of Boronic Acid Terminated Dendrimers

4-Carboxyphenylboronic acid N-hydroxysuccinimide ester

To a solution of 4-carboxyphenylboronic acid (500 mg.) in dry dimethyl formamide (5 ml) were added N-hydroxysuccinimide (380 mg.) and dicyclohexylcarbodiimide (680 mg) The mixture was stirred at 20° C. for 64 hours then the white precipitate was filtered off. The solvent was removed under vacuum and the residue dissolve in ethyl acetate (100 ml.). This solution was washed with water, dried over sodium sulphate and evaporated to give a white solid which was crystallised from acetonitrile/water as fine needles 730 mg. 92%

PAMAM [EDA] 4.0 [4-benzamidoboronic acid]$_{32}$ BRI 6160

To a solution of the PAMAM [EDA] 4.0 (69 mg.) in dry dimethyl sulphoxide (5 ml) under an inert atmosphere was added 4-carboxyphenylboronic acid N-hydroxysuccinimide ester (130 mg.) and the solution stirred for 65 hours at 20° C. To the thick slurry was added 1M sodium carbonate solution (1 ml.) and the clear solution stirred an additional 24 hours. The solvent was removed under vacuum and the residue was dissolved in 10% ammonia solution (5 ml.). This solution was subjected to size exclusion chromatography on Sephadex LH20 eluting with 10% ammonia solution. On evaporation of solvent, the product, PAMAM [EDA] 4.0 [4-benzamidoboronic acid]$_{32}$ was obtained as a white fluffy solid. 110 mg. 94%.

EXAMPLE 31

Preparation of Sodium 3,6-disulfonaphthylthiourea Terminated Dendrimers

BHAlyslys$_2$lys$_4$lys$_8$lys$_{16}$lys$_{32}$

Trifluoroacetic acid (2 ml) was added to a stirred suspension of BHAlyslys$_2$lys$_4$lys$_8$lys$_{16}$DBL$_{32}$ (147 mg) in dry dichloromethane (2 ml) and the resulting solution stirred at room temperature under nitrogen for two hours and then concentrated. The residue was dissolved in N,N-dimethyl-N-allylamine buffer (pH 9.5; 5 ml) and then solid 3,6-disulfonaphthyl isothiocyanate (400 mg) added. The pH of the mixture was then adjusted to 9.5 by the addition of 1M sodium carbonate and the solution heated at 53° C. for three hours under nitrogen. The reaction mixture was concentrated and the residue redissolved in water and the solution passed through a column of Amberlite IR 120 (Na). The filtrate was concentrate was concentrated to give the crude product, which was purified by gel filtration (Sephadex LH20; water) to give BHAlyslys$_2$lys$_4$lys$_8$lys$_{16}$lys$_{32}$ with 64 sodium 3,6-disulfonaphthylurea groups as a white fluffy solid (175 mg).

EXAMPLE 32

Preparation of Sodium 3,5-Disulfophenylthiourea Terminated Dendrimers

BHAlyslys$_2$lys$_4$lys$_8$lys$_{16}$lys$_{32}$

Trifluoroacetic acid (3 ml) was added to a stirred suspension of BHAlyslys$_2$lys$_4$lys$_8$lys$_{16}$DBL$_{32}$ (300 mg; 0.02 mmol) in dry dichloromethane (3 ml) and the resulting solution stirred at room temperature under nitrogen for two hours and then concentrated. The residue was dissolved in water and the solution passed through a column of Amberlite IRA 401 (OH) and the filtrate concentrated to give a viscous oil (187 mg). The oil was dissolved in a 1:1 mixture of pyridine/water (8 ml) and solid sodium 3,5-disulfophenyl isothiocyanate (680 mg; 2 mmol) added. The resulting solution was heated at 53° C. for three hours under nitrogen. The solution was then concentrated to give a white solid residue. The crude product was purified by gel filtration (Sephadex LH20; water) to give BHAlyslys$_2$lys$_4$lys$_8$lys$_{16}$lys$_{32}$ with 64 sodium 3,6-disulfophenylurea groups as a white fluffy solid.

EXAMPLE 33

Preparation of Sodium 3,5-Dicarboxyphenylthiourea Terminated Dendrimers BHAlyslys$_2$lys$_4$lys$_8$lys$_{16}$lys$_{32}$ Trifluoroacetic acid (3 ml) was added to a stirred suspension of BHAlyslys$_2$lys$_4$lys$_8$lys$_{16}$DBL$_{32}$ (300 mg; 0.02 mmol) in dry dichloromethane (3 ml) and the resulting solution stirred at room temperature under nitrogen for two hours and then concentrated. The residue was dissolved in water and the solution passed through a column of Amberlite IRA 401 (OH) and the filtrate concentrated to give a viscous oil (186 mg). The oil was dissolved in a 1:1 mixture of pyridine/water (8 ml) and sodium 3,5-dicarboxyphenyl isothiocyanate (450 mg; 2 mmol) added. The resulting solution was heated at 53° C. for 13 hours under nitrogen. The solution was then concentrated to give a white solid residue. The crude product was purified by gel filtration (Sephadex LH20; water) to give BHAlyslys$_2$lys$_4$lys$_8$lys$_{16}$lys$_{32}$ with 64 sodium 3,6-dicarboxyphenylurea groups as a white fluffy solid.

EXAMPLE 34

Preparation of Sodium 4-phosphonooxyphenylthiourea Terminated Dendrimers BHAlyslys$_2$lys$_4$lys$_8$lys$_{16}$lys$_{32}$ Trifluoroacetic acid (2 ml) was added to a stirred suspension of BHAlyslys$_2$lys$_4$lys$_8$lys$_{16}$DBL$_{32}$ (147 mg; 0.01 mmol) in dry dichloromethane (2 ml) and the resulting solution stirred at room temperature under nitrogen for two hours and then concentrated to give a viscous oil. The oil was dissolved in N,N-dimethyl-N-allylamine buffer (pH 9.5; 5 ml) and solid 4-phosphonooxyphenyl isothiocyanate (250 mg) added. The pH of the resulting solution was adjusted to 10 with 1M sodium carbonate and the mixture heated at 53° C. for three hours under nitrogen. The solution was then concentrated to give a white solid residue. The residue was redissolved in water and the solution passed through a column of Amberlite IR 120 (Na) and the filtrate concentrated. The residue was then purified by gel filtration (Sephadex LH20; water) to give BHAlyslys$_2$lys$_4$lys$_8$lys$_{16}$lys$_{32}$ with 64 sodium 4-phosphonooxyphenylurea groups as a white fluffy solid (150 mg).

EXAMPLE 35

Preparation of Sodium 4-phosphonophenylthiourea Terminated Dendrimers BHAlyslys$_2$lys$_4$lys$_8$lys$_{16}$lys$_{32}$ Trifluoroacetic acid (2 ml) was added to a stirred suspension of BHAlyslys$_2$lys$_4$lys$_8$lys$_{16}$DBL$_{32}$ (147 mg; 0.01 mmol) in dry dichloromethane (2 ml) and the resulting solution stirred at room temperature under nitrogen for two hours and then concentrated to give a viscous oil. The oil was dissolved in N,N-dimethyl-N-allylamine buffer (pH 9.5; 5 ml) and solid 4-phosphonophenyl isothiocyanate (250 mg) added. The pH of the resulting solution was adjusted to 9 with saturated sodium bicarbonate solution and the mixture heated at 53 ° C. for three hours under nitrogen. The solution was then concentrated to give a white solid residue. The residue was redissolved in water and the solution passed through a column of Amberlite IR 120 (Na) and the filtrate concentrated. The residue was then purified by gel filtration (Sephadex LH20; water) to give BHAlyslys$_2$lys$_4$lys$_8$lys$_{16}$lys$_{32}$ with 64 sodium 4-phosphonophenylurea groups BRI 6196 as a white fluffy solid (152 mg) after freeze drying.

EXAMPLE 36

Preparation of Sodium 4,6-diphosphononaphthylthiourea Terminated Dendrimers PAMAM 4.0

A solution of sodium 4,6-diphosphononaphthyl isothiocyanate (165 mg) in water (2 ml) was added to a solution of PAMAM 4.0 (51 mg; 0.01 mmol) in water (2 ml). The pH of the mixture was adjusted to 9.5 with saturated sodium bicarbonate solution and the mixture vigorously stirred for one hour at room temperature and then heated at 53° C. for three hours under nitrogen. The mixture was then filtered and the filtrate concentrated to give a brown solid residue. The crude product was purified by gel filtration (Sephadex G25; water) to give PAMAM 4.0 terminated with 24 sodium 4,6-diphosphononaphthylthiourea groups as a brown solid (81 mg) after freeze drying.

EXAMPLE 37

Preparation of Fluoresceinthiourea Terminated Dendrimers PAMAM 4.0 (EDA)

Solid fluorescein isothiocyanate (188 mg) was added to a solution of PAMAM 4.0 (EDA) (74 mg; 0.01 mmol) in water (3 ml). Saturated sodium bicarbonate solution was added to adjust the pH to 9 and the resulting homogenous solution stirred overnight at room temperature and then concentrated. The orange residue was purified by gel filtration (Sephadex LH20; water) to give PAMAM 4.0 (EDA) terminated with 21 fluoresceinthiourea groups as a fluffy orange solid (193 mg) after freeze drying.

EXAMPLE 38

Preparation of Sodium (phenyl-3-boronic acid)-thiourea Terminated Dendrimers PAMAM 4.0 (EDA)

Solid (phenyl-3-boronic acid) isothiocyanate (100 mg; 0.5 mmol) was added to a solution of PAMAM 4.0 (EDA) (69 mg; 0.01 mmol) in water (5 ml). 1M sodium carbonate was added to the isothiocyanate dissolved (pH ca.10). The mixture was then heated at 53° C. for two hours under nitrogen, and then filtered and the filtrate concentrated to give a brownish solid residue. The crude product was purified by gel filtration (Sephadex LH20; water) to give PAMAM 4.0 (EDA) terminated with 32 (phenyl-3-boronic acid)thiourea groups as a white fluffy solid (87 mg) after freeze drying.

EXAMPLE 39

Preparation of Sodium 3,5-Dicarboxyphenylthiourea Terminated Polylysines

A solution of poly-L-lysine.hydrobromide (4–15K) (Sigma Chemical Company) (50 mg) in water (2 ml) was added to a solution of sodium 3,5-dicarboxyphenyl isothiocyanate (305 mg) in water (3ml) and the pH of the resulting solution adjusted to 9 with aqueous sodium bicarbonate. The solution was then heated at 53° C. under nitrogen for 4 hours. The solution was cooled and filtered, and the filtrate concentrated to give an off-white solid residue. The crude product was purified by gel filtration (Sephadex LH20; water) and freeze dried to give sodium 3,5-dicarboxyphenylthiourea terminated poly-L-lysine as a white fluffy solid (71 mg).

EXAMPLE 40

Preparation of Sodium 4-(Phosphonomethyl) phenylthiourea Terminated Polylysines

Solid 4-(phosphonomethyl)phenyl isothiocyanate (231 mg; 1.0 mmol) was added to a solution of poly-L-lysine.hydrobromide (30–70K) (Sigma Chemical Company) (50 mg) in a 1:1 mixture of pyridine/water. The pH of the mixture was adjusted to 9.5 with 1M sodium carbonate and the solution heated overnight at 53° C. under nitrogen. The mixture was cooled and filtered, and the filtrate concentrated to give a brown solid residue. The crude product was purified by gel filtration (Sephadex LH20; water) to a give a brown solid (82 mg).

EXAMPLE 41

Preparation of 1-phosphono-oxyphenyl-4-thiourea Terminated poly-L-lysine

To a solution of poly-L-lysine hydrobromide (50 mg; Sigma P2636, 30–70 kilodaltons) in water (10 ml), heated and stirred at 53° C., was added 4-phosphonooxyphenylisothiocyanate (153 mg) and the pH of the mixture adjusted to 9.5–10 with 1M sodium carbonate solution. The mixture was heated and stirred at 53° C. for 5 hours and then filtered. The clear solution was purified by gel filtration on Sephadex LH20 eluting with water. The eluent was lyophilised to give the product as a white foam. 77 mg. 94%.

EXAMPLE 42

Preparation of benzamido-4-boronic acid Terminated poly-L-lysine

To a solution of poly-L-lysine hydrobromide (50 mg; Sigma P2636, 30–70 kilodaltons) in DMSO (10 ml), under an inert atmosphere, was added 4-carboxyphenylboronic acid N-hydroxysuccinimide ester (90 mg) and 1M sodium carbonate solution (2 ml) and the mixture stirred at 20° C. for 60 hours. Solvent was removed in vacuo and the residue dissolved in water (5 ml) and filtered. The clear solution was purified by gel filtration on Sephadex LH20 eluting with water. The eluent was lyophilised to give the product as a white foam. 50 mg. 90%.

EXAMPLE 43

I. Chorioallantioic Membrane (CAM) Assay

The in vivo CAM angiogenesis model, initially described by Folkman (1985) and modified by Maragoudakis et al (1988) was used. Briefly, fresh fertilized eggs were incubated for 4 days at 37° C. when a window was opened on the egg shell exposing the CAM. The window was covered with cellophane tape and the eggs were returned to the incubator until day 9 when the test compounds were applied. The test compounds were placed on sterile plastic discs (10 mm) and were allowed to dry under sterile conditions. Control discs (containing PBS) were placed on the CAM 1 cm away from the discs containing the test material. A sterile solution of cortisone acetate (100 ug/disc, Sigma) was incorporated in all discs in order to prevent an inflammatory response. The loaded and dried discs were inverted and placed on the CAM, the windows were covered and the eggs incubated until day 11 when angiogenesis was assessed.

Morphological Evaluation of Angiogenesis in the CAM Assay

For morphological evaluation, eggs were treated as above. At day 11 the eggs were flooded with 10% buffered formalin (Janssen Chimica, Geel, Belguim), the plastic discs were removed and the eggs were kept at room temperature for at least 4 hours. At large area around the disc was cut off and placed on a glass slide, and the vascular density index (expressed as number of blood vessels) was measured by the method of Harris-Hooker et al (1983).

II. Rat Aorta Assay

The rat aorta ring model, initially described by Nicosia et al, (1990) was used. Briefly, a sterile 1.5% solution of agarose (Pharmacia Biotech AB, Upppsala, Sweden) was poured into culture dishes and allowed to gel. Agarose rings were obtained by punching two concentric circles, with diameter of 10 and 17 mm, respectively, in the agarose gel. The excess agarose inside and outside the rings was removed. The rings were transferred to a 6-well plate (Nuncion, Roskilde, Denmark), each well containing three rings. Thoracic aortas were obtained from 3-month-old male Wistar rats. The aortas were immediately transferred to a culture disk with serum-free Minimal Essential Medium (MEM). The fibroadipose tissue around the aorta was carefully removed in order to damage the aortic wall. Thin slices (0.5 mm thick) of aortic rings were sectioned and extensively rinsed in 12 consecutive washes of serum-free medium. Before transferring the aortic rings to the culture rings in the culture plate, the bottom of each agarose well was coated with 150 ul of clotting fibrinogen. After the fibrin gel had formed, the aortic ring was transferred to the agarose well and positioned in the center of the agarose well. Then the agarose wells were completely filled with clotting fibrinogen. Partially purified bovine fibrinogen (Sigma) was dissolved in serum-free medium in order to obtain a concentration of 3 mg/ml. Clotting was obtained by adding 20 ul of a 50 $\mu$l/ml bovine thrombin solution (Sigma) to 1 ml of fibrinogen solution. The fibrin gel formed within 30 seconds at room temperature. After fibrin gelation, 6 ml of MEM medium, supplemented with 20% PCS (Gibco), 10M Hepes (Gibco) and 1 mM L-glutamine (Gibco), were added to each well of the 6-well plate and the test compound was added to the medium at the appropriate concentration.

Quantitation of Angiogenesis for the Rat Aorta Ring Assay

Cultures were examined daily and scored under an inverted microscope. The growth of microvessels is represented by means of a microvascular growth curve. Formation of more than 200 to 250 microvessels is common (Nicosia et al 1990) due to the three-dimensional complexity of the microvascular network. The margin of error for the observer who is counting the microvessels is high: therefore, the formed microvessels were scored on a scale from 0 (no vessels) to 10 (maximum vessel number).

Results

I. CAM Assay

| egg no | BRI6112 (25 μg/cam) | BRI2923 (25 μg/cam) | BRI2995 (25 μg/cam) | BRI2784 (25 μg/cam) | BRI6039 (25 μg/cam) |
|---|---|---|---|---|---|
| 1 | −11% | −45% | −36% | 0 | +11% |
| 2 | −13% | −17% | −22% | −7% | −33% |
| 3 | −26% | −35% | −54% | −36% | −9% |
| 4 | +11% | −87% | −73% | +10% | −34% |
| 5 | −42% | −48% | −55% | −40% | −26% |
| 6 | −41% | −8% | −43% | −27% | −27% |
| 7 | −32% | −57% | −34% | 0 | −12% |
| 8 | −15% | | −20% | −27% | −18% |
| 9 | 0 | | −22% | −36% | −63% |
| 10 | −57% | | −88% | −54% | −53% |
| 11 | | | +23% | 0 | −16% |
| 12 | | | −30% | −57% | +43% |
| 13 | | | 0 | | |
| x = | −22.6 ± 20.9 | −42.4 ± 26.2 | −34.9 ± 29.3 | −22.8 ± 22.8 | −19.8 ± 27.8 |
| | P ≤ 0.01 | p ≤ 0.05 | p ≤ 0.01 | p ≤ 0.05 | p ≤ 0.05 |

*Higher concentrations (50 μg/cam) of BRI2995 and BRI6112 have been evaluated: BRI2995 cause 50% embryo death. The surviving eggs showed 73% inhibition of vascular density. No toxicity was found for BRI6112 at this concentration. However only a slight inhibition of vascular density (−16%) was observed.

TNP-470 (50 μ/cam) and Pentosan Polysulphate (PPS) (50 μg), two compounds that are in clinical trial, were included as reference compounds. They reduced vascular density by respectively 21%±16 and 42%±28. PPS caused however 80% embryo death at this concentration.

II. RAT-aorta Assay

BRI2995, BRI2996 and BRI2999 (almost) completely inhibited the formation of microvessels at concentrations of 20 μg/ml and 100 μg/ml.

BRI6196 gave nearly complete inhibition at 20 μg/ml and 100 μmg/ml, and also gave inhibition at 4 μg/ml.

BRI2923 and BRI6039 reduced microvessel growth at a concentration of 100 μg/ml.

REFERENCES

1. Folkman J. (1985) J. Biol. Chem. 267:10931–10934.
2. Harris-Hooker S. A. et al (1983) J. Cell. Physiol. 114:302–310.
3. Hasegawa A. et al (1986) J. Carbohydrate Chemistry. 5(1):11–19.
4. Maragoudakis M. E. et al (1988) Tissue Cell. 20:531–539.
5. Nicosia R. F. and Ottinetti A. (1990) Cell Dev. Bio. 26:119–128.
6. Sabesan S. (1994) Bio-Organic and Medicinal Chemistry Letters. 4 (20):2457–2460.

What is claimed is:

1. A method of prophylactic or therapeutic inhibition of angiogenesis in a patient, which comprises administering to the patient of an effective amount of at least one compound sufficient to inhibit or prevent angiogenesis, wherein said compound is a dendrimer having a plurality of terminal groups and wherein at least one of said terminal groups has an anionic- or cationic-containing moiety bonded or linked thereto.

2. The method according to claim 1, wherein said compound is a dendrimer which comprises a polyvalent core covalently bonded to at least two dendritic branches, and wherein said dendrimer extends through at least two generations.

3. The method according to claim 1 wherein said dendrimer is a polyamidoamine dendrimer based on an ammonia core.

4. The method according to claim 1 wherein said dendrimer is a polyamidoamine dendrimer based on an ethylene diamine core.

5. The method according to claim 1 wherein said dendrimer is a polylysine dendrimer based on a benzhydrylamine core.

6. The method according to claim 1 wherein said compound is a polyionic dendrimer of the formula:

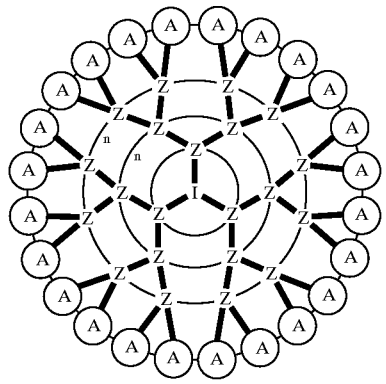

wherein:
I is an initiator core;
Z is an interior branching unit;
n is an integer which represents the number of generations of the dendrimer, and
A is an anionic-containing moiety which may be linked to interior branching unit Z through an optional linking group X.

7. The method according to claim 1 wherein said anionic or cationic containing moiety is bonded to a reactive functional terminal group of the dendrimer by amide or thiourea linkages.

8. The method according to claim 7 wherein said reactive functional is a terminal group selected from the group consisting of an amine moiety, a sulfhydryl moiety, and a hydroxy moiety.

9. The method according to claim 1 wherein said anionic-containing moiety is selected from the group consisting of a sulfonic acid containing moiety, a carboxylic acid containing moiety, a neuraminic acid containing moiety, a sialic acid-containing moiety, a modified neuraminic acid containing moiety, a modified sialic acid containing moiety, a boronic acid containing moiety, a phosphoric acid containing moiety, a phosphonic acid containing moiety, an esterified phosphoric acid containing moiety, and an esterified phosphonic acid containing moiety.

10. The method according to claim 1 wherein the moiety which is bonded to said terminal groups is selected from the group consisting of
—NH(CH$_2$)$_n$SO$_3$;
—(CH$_2$)—SO$_3$;
—(CH$_2$)—SO$_3$;
—Ar(SO$_3$)$_n$;
—CH$_2$CH(SO$_3$)COOH;
—CH(SO$_3$)CH$_2$COOH;
—ArX$^1$(CH$_2$)$_n$SO$_3$;
—(CH$_2$)$_{n+}$NMe$_3$;
—Ar(N+Me$_3$)$_n$;
—Ar(CH$_2$N+Me$_3$)$_n$;
—ArX$^2$P(=O)(OR)$_2$;
—ArX$^2$P(=O)(OR)(NR$^1$R$^1$);
—Ar[P(=O)(OR)$_2$]$_{n1}$;
—Ar[B(OH)$_2$]$_{n1}$
—Ar[COOH]$_{n1}$

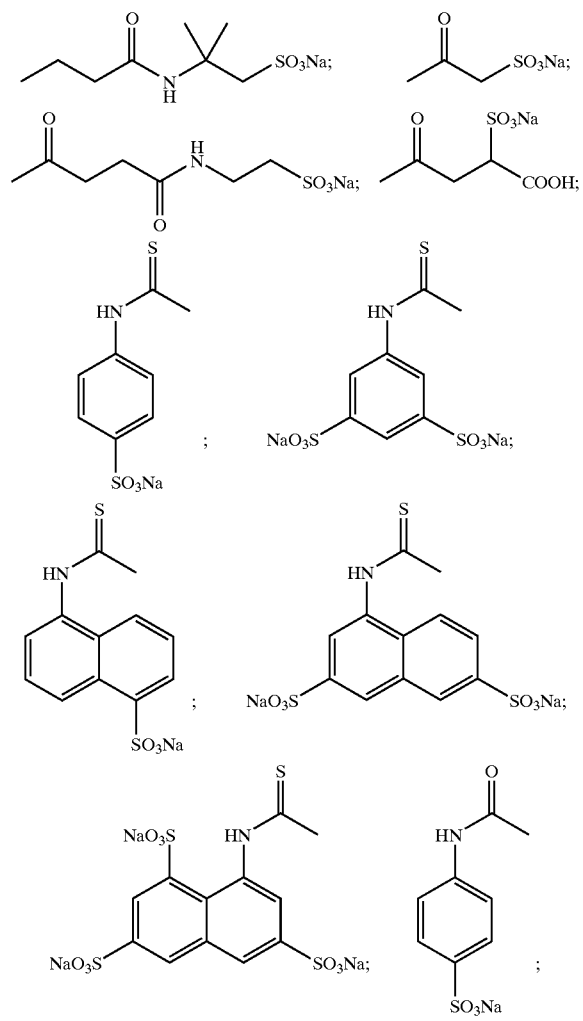

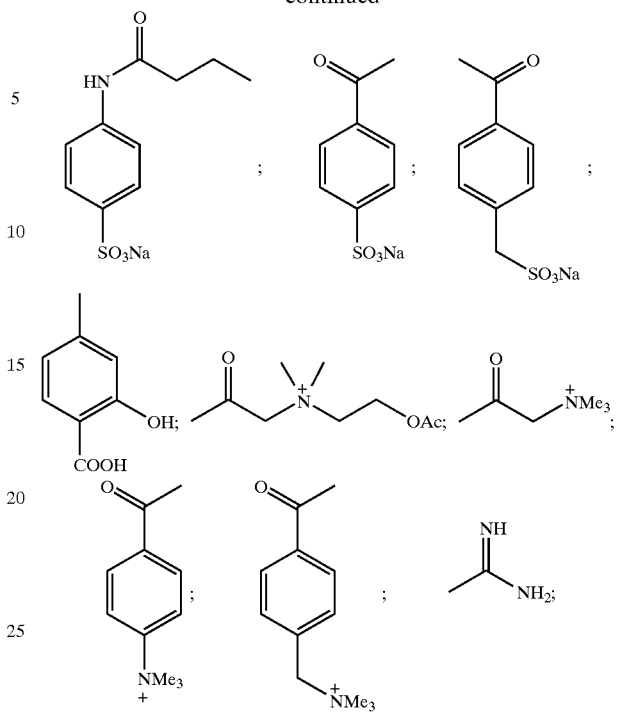

wherein n is zero or a positive integer;
wherein n1 is 1, 2 or 3;
wherein R is alkyl, aryl, H or Na;
wherein R$^1$ is alkyl or aryl;
wherein X$^1$ is O, S, or NH; and
wherein X$^2$ is O, CH$_2$, CHF, or CF$_2$.

11. The method according to claim 1 wherein said compound is selected from the group consisting of
an alkylsulfonic acid terminated dendrimer,
a sulfoacetamide terminated dendrimer,
a sulfosuccinamic acid terminated dendrimer,
a N-(2-sulfoethyl)succinamide terminated dendrimer,
a 4-sulfophenylthiourea terminated dendrimer,
a 3,6-di-sulfonaphthylthiourea terminated dendrimer,
a 4-sulfonaphthylthiourea terminated dendrimer,
a 3,5-di-sulfophenylthiourea terminated dendrimer,
a 3,6,8-tri-sulfonaphthylthiourea terminated dendrimer,
a 4-(sulfomethyl)benzamide terminated dendrimer,
a 4-sulfobenzamide terminated dendrimer,
a N-(4-sulfophenyl)propanamide terminated dendrimer,
a 4-sulfophenylurea terminated dendrimer,
a N,N,N-tri-methylglycinamide terminated dendrimer,
a 4-trimethylammonium benzamide terminated dendrimer,
a 4-(trimethylammoniumethyl)benzamide terminated dendrimer,
a N-(2-acetoxyethyl)-N,N-(dimethylammonium)methyl-carboxamide terminated dendrimer,
a guanidino terminated dendrimer,
a 4-([1,4,8,11-tetraazacyclotetradecane]methyl)benzamide terminated dendrimer,
a 4-carboxy-3-hydroxy-benzylamine terminated dendrimer,
a 4-carboxyphenylamide terminated dendrimer,
a 3,5-dicarboxyphenylamide terminated dendrimer,
a 4-phosphonooxyphenylthiourea terminated dendrimer,
a 4-(phosphonomethyl)phenylthiourea terminated dendrimer,
an ethyl-4-(phosphonomethyl)phenylthiourea terminated dendrimer, an (8-octanamido)-5-acetamido-3,5-dideoxy-2-thio-D-glycero-α-D-galacto-2-nonulopyranosidoic acid terminated dendrimer,
an (11-undecanamido)-5-acetamido-3,5-dideoxy-2-thio-D-glycero-α-D-galacto-2-nonulopyranosidoic acid terminated dendrimer,
an (acetamido)-5-acetamido-3,5-dideoxy-2-thio-D-glycero-α-D-galacto-2-nonulopyranosidoic acid terminated dendrimer,
a (4-butanamido)-5-acetamido-3,5-dideoxy-2-thio-D-glycero-α-D-galacto-2-nonulopyranosidoic acid terminated dendrimer,
a (4-methylbenzamido)-5-acetamido-3,5-dideoxy-2-thio-D-glycero-α-D-galacto-2-nonulopyranosidoic acid terminated dendrimer,
an (8-octanamido)-4-azido-5-acetamido-3,4,5-trideoxy-2-thio-D-glycero-α-D-galacto-2-nonulopyranosidoic acid terminated dendrimer,
an (8-octanamido)-4-amino-5-acetamido-3,4,5-trideoxy-2-thio-D-glycero-α-D-galacto-2-nonulopyranosidoic acid terminated dendrimer,
a 4-benzamidoboronic acid terminated dendrimer,
a 3,5-dicarboxyphenylthiourea terminated dendrimer,
a 4-phosphonophenylthiourea terminated dendrimer,
a 4,6-diphosphononaphthylthiourea terminated dendrimer,
a fluoresceinthiourea terminated dendrimer, and
a (phenyl-3-boronic acid)-thiourea terminated dendrimer.

12. The method according to claim 2 wherein said compound is selected from the group consisting of
an alkylsulfonic acid terminated dendrimer,
a sulfoacetamide terminated dendrimer,
a sulfosuccinamic acid terminated dendrimer,
a N-(2-sulfoethyl)succinamide terminated dendrimer,
a 4-sulfophenylthiourea terminated dendrimer,
a 3,6-di-sulfonaphthylthiourea terminated dendrimer,
a 4-sulfonaphthylthiourea terminated dendrimer,
a 3,5-di-sulfophenylthiourea terminated dendrimer,
a 3,6,8-tri-sulfonaphthylthiourea terminated dendrimer,
a 4-(sulfomethyl)benzamide terminated dendrimer,
a 4-sulfobenzamide terminated dendrimer,
a N-(4-sulfophenyl)propanamide terminated dendrimer,
a 4-sulfophenylurea terminated dendrimer,
a N,N,N-tri-methylglycinamide terminated dendrimer,
a 4-trimethylammonium benzamide terminated dendrimer,
a 4-(trimethylammoniummethyl)benzamide terminated dendrimer,
a N-(2-acetoxyethyl)-N,N-(dimethylammonium)methylcarboxamide terminated dendrimer,
a guanidino terminated dendrimer,
a 4-([1,4,8,11-tetraazacyclotetradecane]methyl)benzamide terminated dendrimer,
a 4-carboxy-3-hydroxy-benzylamine terminated dendrimer,
a 4-carboxyphenylamide terminated dendrimer,
a 3,5-dicarboxyphenylamide terminated dendrimer,
4-phosphonooxyphenylthiourea terminated dendrimer,
a 4-(phosphonomethyl)phenylthiourea terminated dendrimer,
an ethyl-4-(phosphonomethyl)phenylthiourea terminated dendrimer,
an (8-octanamido)-5-acetamido-3,5-dideoxy-2-thio-D-glycero-α-D-galacto-2-nonulopyranosidoic acid terminated dendrimer,
an (11-undecanamido)-5-acetamido-3,5-dideoxy-2-thio-D-glycero-α-D-galacto-2-nonulopyranosidoic acid terminated dendrimer,
an (acetamido)-5-acetamido-3,5-dideoxy-2-thio-D-glycero-α-D-galacto-2-nonulopyranosidoic acid terminated dendrimer,
a (4-butanamido)-5-acetamido-3,5-dideoxy-2-thio-D-glycero-α-D-galacto-2-nonulopyranosidoic acid terminated dendrimer,
a (4-methylbenzamido)-5-acetamido-3,5-dideoxy-2-thio-D-glycero-α-D-galacto-2-nonulopyranosidoic acid terminated dendrimer,
an (8-octanamido)-4-azido-5-acetamido-3,4,5-trideoxy-2-thio-D-glycero-α-D-galacto-2-nonulopyranosidoic acid terminated dendrimer,
an (8-octanamido)-4-amino-5-acetamido-3,4,5-trideoxy-2-thio-D-glycero-α-D-galacto-2-nonulopyranosidoic acid terminated dendrimer,
a 4-benzamidoboronic acid terminated dendrimer,
a 3,5-dicarboxyphenylthiourea terminated dendrimer,
a 4-phosphonophenylthiourea terminated dendrimer,
a 4,6-diphosphononaphthylthiourea terminated dendrimer,
a fluoresceinthiourea terminated dendrimer, and
a (phenyl-3-boronic acid)-thiourea terminated dendrimer.

13. The method according to claim 1 wherein said patient suffers from a disorder involving inappropriate growth of blood vessels.

14. The method according to claim 1 wherein said patient suffers from restenosis, a wound in need of healing, or a cancer.

15. The method according to claim 1 where said patient suffers from a chronic inflammatory disorder, diabetic retinopathy, psoriasis or rheumatoid arthritis.

16. A pharmaceutical composition for preventing or inhibiting angiogenesis in a human or nonhuman animal, which comprises (a) a dendrimer having a plurality of terminal groups wherein at least one of said terminal groups has an anionic- or cationic-containing moiety bonded or linked thereto in association with (b) at least one pharmaceutically acceptable carrier or diluent.

17. A process for making a composition useful in preventing or inhibiting angiogenesis comprising combining (a) a dendrimer having a plurality of terminal groups wherein at least one of said terminal groups has an anionic- or cationic-containing moiety bonded or linked thereto with (b) a pharmaceutically acceptable carrier or diluent.

18. A dendrimer having a plurality of terminal groups, wherein at least one of said terminal groups is bonded to or linked to an anionic-containing moiety, and wherein said anionic-containing moiety is selected from the group consisting of
a neuraminic acid containing moiety,
a sialic acid containing moiety,
a neuraminic acid containing moiety that is modified by substitution in the 4-position with an amino, amido, cyano, azido or guanidino group,
a sialic acid containing moiety that is modified by substitution in the 4-position with an amino, amido, cyano, azido or guanidino group,
a boronic acid containing moiety,
a phosphoric acid containing moiety,
a phosphonic acid-containing moiety,
an esterified phosphoric acid containing moiety, and
an esterified phosphonic acid containing moiety.

19. A dendrimer comprising
a polyvalent core covalently bonded to at least two dendritic branches;
a plurality of terminal groups wherein at least one of said terminal groups has an anionic- or cationic-containing moiety bonded or linked thereto;
wherein said dendrimer extends through at least two generations;

and wherein said dendrimer is selected from the group consisting of:

an alkylsulfonic acid terminated dendrimer,
a sulfoacetamide terminated dendrimer,
a sulfosuccinamic acid terminated dendrimer,
a N-(2-sulfoethyl)succinamide terminated dendrimer,
a 4-sulfophenylthiourea terminated dendrimer,
a 3,6-di-sulfonaphthylthiourea terminated dendrimer,
a 4-sulfonaphthylthiourea terminated dendrimer,
a 3,5-di-sulfophenylthiourea terminated dendrimer,
a 3,6,8-tri-sulfonaphthylthiourea terminated dendrimer,
a 4-(sulfomethyl)benzamide terminated dendrimer,
a 4-sulfobenzamide terminated dendrimer,
a N-(4-sulfophenyl)propanamide terminated dendrimer,
a 4-sulfophenylurea terminated dendrimer,
a N,N,N-tri-methylglycinamide terminated dendrimer,
a 4-trimethylammonium benzamide terminated dendrimer,
a 4-(trimethylammoniummethyl)benzamide terminated dendrimer,
a N-(2-acetoxyethyl)-N,N-(dimethylammonium)methylcarboxamide terminated dendrimer,
a guanidino terminated dendrimer,
a 4-([1,4,8,11-tetraazacyclotetradecane]methyl)benzamide terminated dendrimer,
a 4-carboxy-3-hydroxy-benzylamine terminated dendrimer,
a 4-carboxyphenylamide terminated dendrimer,
a 3,5-dicarboxyphenylamide terminated dendrimer,
4-phosphonooxyphenylthiourea terminated dendrimer,
a 4-(phosphonomethyl)phenylthiourea terminated dendrimer,
an ethyl-4-(phosphonomethyl)phenylthiourea terminated dendrimer,
an (8-octanamido)-5-acetamido-3,5-dideoxy-2-thio-D-glycero-α-D-galacto-2-nonulopyranosidoic acid terminated dendrimer,
an (11-undecanamido)-5-acetamido-3,5-dideoxy-2-thio-D-glycero-α-D-galacto-2-nonulopyranosidoic acid terminated dendrimer,
an (acetamido)-5-acetamido-3,5-dideoxy-2-thio-D-glycero-α-D-galacto-2-nonulopyranosidoic acid terminated dendrimer,
a (4-butanamido)-5-acetamido-3,5-dideoxy-2-thio-D-glycero-α-D-galacto-2 -nonulopyranosidoic acid terminated dendrimer,
a (4-methylbenzamido)-5-acetamido-3,5-dideoxy-2-thio-D-glycero-α-D-galacto-2-nonulopyranosidoic acid terminated dendrimer,
an (8-octanamido)-4-azido-5-acetamido-3,4,5-trideoxy-2-thio-D-glycero-α-D-galacto-2-nonulopyranosidoic acid terminated dendrimer, an (8-octanamido)-4-amino-5-acetamido-3,4,5-trideoxy-2-thio-D-glycero-α-D-galacto-2-nonulopyranosidoic acid terminated dendrimer,
a 4-benzamidoboronic acid terminated dendrimer,
a 3,5-dicarboxyphenylthiourea terminated dendrimer,
a 4-phosphonophenylthiourea terminated dendrimer,
a 4,6-diphosphononaphthylthiourea terminated dendrimer,
a fluoresceinthiourea terminated dendrimer, and
a (phenyl-3-boronic acid)-thiourea terminated dendrimer.

20. The dendrimer according to claim 1, further comprising a polyvalent core covalently bonded to at least two dendritic branches, and wherein said dendrimer extends through at least two generations.

21. The dendrimer according to claim 1, further comprising a polyamidoamine dendrimer based on an ammonia core.

22. The dendrimer according to claim 1, further comprising a polyamidoamine dendrimer based on an ethylene diamine core.

23. The dendrimer according to claim 1, wherein said dendrimer is a polylysine dendrimer based on a benzhydrylamine or other suitable core.

24. The dendrimer according to claim 1, wherein said anionic-containing moiety is bonded to a reactive functional terminal group of said dendrimer by amide or thiourea linkages.

25. The dendrimer according to claim 1, wherein said dendrimer is selected from the group consisting of
a 4-phosphonooxyphenylthiourea terminated dendrimer,
a 4-(phosphonomethyl)phenylthiourea terminated dendrimer,
an ethyl-4-(phosphonomethyl)phenylthiourea terminated dendrimer,
an (8-octanamido)-5-acetamido-3,5-dideoxy-2-thio-D-glycero-α-D-galacto-2-nonulopyranosidoic acid terminated dendrimer,
an (11-undecanamido)-5-acetamido-3,5-dideoxy-2-thio-D-glycero-α-D-galacto-2-nonulopyranosidoic acid terminated dendrimer,
an (acetamido)-5-acetamido-3,5-dideoxy-a 2-thio-D-glycero-α-D-galacto-2-nonulopyranosidoic acid terminated dendrimer,
a (4-butanamido)-5-acetamido-3,5-dideoxy-2-thio-D-glycero-α-D-galacto-2-nonulopyranosidoic acid terminated dendrimer,
a (4-methylbenzamido)-5-acetamido-3,5-dideoxy-2-thio-D-glycero-α-D-galacto-2-nonulopyranosidoic acid terminated dendrimer,
an (8-octanamido)-4-azido-5-acetamido-3,4,5-trideoxy-2-thio-D-glycero-α-D-galacto-2-nonulopyranosidoic acid terminated dendrimer,
an (8-octanamido)-4-amino-5-acetamido-3,4,5-trideoxy-2-thio-D-glycero-α-D-galacto-2-nonulopyranosidoic acid terminated dendrimer,
a 4-benzamidoboronic acid terminated dendrimer,
a 4-phosphonophenylthiourea terminated dendrimer,
a 4,6-diphosphononaphthylthiourea terminated dendrimer, and
a (phenyl-3-boronic acid)-thiourea terminated dendrimer.

26. The process according to claim 17, wherein the terminal group comprises an amine moiety, a sulfhydryl moiety or a hydroxy moiety.

* * * * *